(12) United States Patent
Harichian et al.

(10) Patent No.: US 9,775,793 B2
(45) Date of Patent: *Oct. 3, 2017

(54) PROLONGED DELIVERY OF CERTAIN FRAGRANCE COMPONENTS FROM PERSONAL CARE COMPOSITIONS

(71) Applicant: Conopco, Inc., Englewood Cliffs, NJ (US)

(72) Inventors: Bijan Harichian, Brookfield, CT (US); Ian Stuart Cloudsdale, Chapel Hill, NC (US); Lin Yang, Woodbridge, CT (US); John Kenneth Dickson, Jr., Apex, NC (US)

(73) Assignee: Conopco, Inc., Englewood Cliffs, NJ (US)

( * ) Notice: Subject to any disclaimer, the term of this patent is extended or adjusted under 35 U.S.C. 154(b) by 138 days.

This patent is subject to a terminal disclaimer.

(21) Appl. No.: 14/771,239

(22) PCT Filed: Mar. 10, 2014

(86) PCT No.: PCT/EP2014/054587
§ 371 (c)(1),
(2) Date: Aug. 28, 2015

(87) PCT Pub. No.: WO2014/139952
PCT Pub. Date: Sep. 18, 2014

(65) Prior Publication Data
US 2016/0015616 A1    Jan. 21, 2016

Related U.S. Application Data

(60) Provisional application No. 61/778,802, filed on Mar. 13, 2013.

(51) Int. Cl.
| | |
|---|---|
| *A61K 8/49* | (2006.01) |
| *A61Q 19/02* | (2006.01) |
| *A61Q 17/04* | (2006.01) |
| *A61K 8/42* | (2006.01) |
| *A61Q 1/02* | (2006.01) |
| *A61Q 13/00* | (2006.01) |
| *A61Q 19/00* | (2006.01) |
| *A61K 8/02* | (2006.01) |
| *A61K 8/06* | (2006.01) |
| *A61K 8/31* | (2006.01) |
| *A61K 8/36* | (2006.01) |
| *A61Q 1/06* | (2006.01) |
| *A61Q 1/10* | (2006.01) |
| *A61Q 9/02* | (2006.01) |
| *A61Q 9/04* | (2006.01) |
| *A61Q 11/00* | (2006.01) |
| *A61Q 15/00* | (2006.01) |
| *A61Q 19/10* | (2006.01) |

(52) U.S. Cl.
CPC .......... *A61K 8/4926* (2013.01); *A61K 8/0208* (2013.01); *A61K 8/064* (2013.01); *A61K 8/31* (2013.01); *A61K 8/36* (2013.01); *A61K 8/42* (2013.01); *A61K 8/49* (2013.01); *A61K 8/4906* (2013.01); *A61K 8/4913* (2013.01); *A61K 8/4973* (2013.01); *A61Q 1/02* (2013.01); *A61Q 1/06* (2013.01); *A61Q 1/10* (2013.01); *A61Q 9/02* (2013.01); *A61Q 9/04* (2013.01); *A61Q 11/00* (2013.01); *A61Q 13/00* (2013.01); *A61Q 15/00* (2013.01); *A61Q 17/04* (2013.01); *A61Q 19/00* (2013.01); *A61Q 19/10* (2013.01)

(58) Field of Classification Search
CPC .... A61K 8/4926; A61K 8/0208; A61K 8/064; A61K 8/31; A61K 8/36; A61K 8/42; A61K 8/49; A61K 8/4906; A61K 8/4913; A61K 8/4973; A61Q 16/00; A61Q 1/02; A61Q 11/00; A61Q 15/00; A61Q 17/04; A61Q 19/10; A61Q 1/06; A61Q 9/02; A61Q 9/04

See application file for complete search history.

(56) References Cited

U.S. PATENT DOCUMENTS

| | | | |
|---|---|---|---|
| 4,940,696 | A | 7/1990 | Shroot et al. |
| 4,956,481 | A | 9/1990 | Gillaspey |
| 4,985,403 | A | 1/1991 | Narula |
| 5,135,747 | A | 8/1992 | Faryniarz |
| 5,212,203 | A | 5/1993 | Shroot |
| 5,212,303 | A | 5/1993 | Shroot |
| 5,833,999 | A | 11/1998 | Trinh |
| 5,849,310 | A | 12/1998 | Trinh |

(Continued)

FOREIGN PATENT DOCUMENTS

| | | |
|---|---|---|
| DE | 10337579 | 4/2004 |
| DE | 10337579 A | 4/2004 |

(Continued)

OTHER PUBLICATIONS

Search Report PCTEP2014054604 dated Jun. 11, 2014.

(Continued)

*Primary Examiner* — Nannette Holloman
(74) *Attorney, Agent, or Firm* — Ellen Plotkin

(57) ABSTRACT

A personal care composition is provided having a highly volatile fragrance which incorporates alpha pinene, beta pinene, hexyl acetate, limonene, (+)-citronellal, dihydromyrcenol, alpha citronellol, beta citronellol, genaniol, lilial or combinations thereof in conjunction with tricyclodecane amide. The tricyclodecane amide functions to prevent fast volatilization of the highly volatile fragrance components when the personal care composition is applied to skin or hair of the human body.

12 Claims, No Drawings

(56) References Cited

U.S. PATENT DOCUMENTS

| | | | |
|---|---|---|---|
| 6,086,903 | A | 7/2000 | Trinh |
| 6,100,233 | A | 8/2000 | Sivik |
| 6,399,045 | B1 | 6/2002 | Morgan |
| 6,576,228 | B1 | 6/2003 | Crookham |
| 7,282,522 | B2 | 10/2007 | Rho et al. |
| 8,053,431 | B2 | 11/2011 | Kilburn |
| 8,173,108 | B2 | 5/2012 | Misso et al. |
| 2003/0003119 | A1 | 1/2003 | Bekele |
| 2004/0228814 | A1 | 11/2004 | Candau |
| 2006/0024337 | A1 | 2/2006 | Simonnet |
| 2006/0057083 | A1 | 3/2006 | Mathonneau |
| 2006/0062746 | A1 | 3/2006 | Brillouet et al. |
| 2006/0166856 | A1 | 7/2006 | Petrat |
| 2011/0104082 | A1 | 5/2011 | Polonka |
| 2011/0104087 | A1 | 5/2011 | Polonka |
| 2012/0004206 | A1 | 1/2012 | Pliushchev |

FOREIGN PATENT DOCUMENTS

| | | |
|---|---|---|
| DE | 10337579 | 4/2014 |
| EP | 0199636 | 2/1989 |
| EP | 1010685 | 6/2000 |
| ES | 2296463 | 4/2008 |
| ES | 2296463 | 2/2009 |
| WO | WO9918919 | 6/1999 |
| WO | WO03075878 | 9/2003 |
| WO | WO2004089415 | 10/2004 |
| WO | WO2004089416 | 10/2004 |
| WO | WO2004089470 | 10/2004 |
| WO | WO2005019162 | 3/2005 |
| WO | WO2006119283 | 11/2006 |
| WO | WO2008054144 | 5/2008 |
| WO | WO2011054704 | 6/2011 |

OTHER PUBLICATIONS

Search Report PCTEP2014054606 dated Jun. 11, 2014.
Written Opinion 1 in PCTEP2014054604 dated Jun. 11, 2014.
Written Opinion 1 in PCTEP2014054606 dated Jun. 11, 2014.
Akhrem et al., "Alkanes and cycloalkanes in the one-pot synthesis of amides", Mendeleev Communications, 2007, vol. 17, pp. 279-280.
Akhrem et al., "The first one-pot amidation of alkanes and cycloalkanes", Tetrahedron Letters, Jan. 10, 2008, vol. 49, pp. 1399-1404.
Kasemura et al., "Miticidal Activity of Monoterpenyl Carboxypyrrolidinamides and Piperidinamides", Journal of Oleo Science, 2003, vol. 52, No. 1, pp. 41-46.
Kontonassios et al., "3-(Dialkylamino)methyladamantane-1-carboxylic Acids", Notes, Apr. 29, 1968, vol. 12, pp. 170-172.
Egan et al., Raoult's law and vapor pressure measurement, Journal of Chemical Education, May 1, 1976, vol. 53, No. 5, p. 303.
Schafer et al., "Facile synthesis of Sterically Hindered and Electron-Deficient Secondary Amides from Isocyanates", Angew. Chem. Int. Edition, Sep. 3, 2012, vol. 51, No. 36, pp. 9173-9175; XP055120011.
Schuster et al., "The Discovery of New 11B-Hydroxysteroid Dehydrogenase Type 1 Inhibitors by Common Feature Pharmacophore Modeling and Virtual Screening", Journal of Medical Chem, 2006, vol. 49, pp. 3454-3466, 49.
Search Report in PCTEP2014054587 dated Oct. 14, 2014.
Terao et al., "11B-Hydroxysteroid Dehydrogenase-1 is a Novel Regulator of Skin Homeostasis and a Candidate Target for Promoting Tissue Repair", PLos One, Sep. 2011, vol. 6 Iss 9, pp. 1-11.
Tiganescu et al., "Localization, Age-and Site-Dependent Expression, and Regulation of 11B-Hydroxysteroid Dehydrogenase Type 1 in Skin", Journal of Invesitgative Dermatology, 2011, vol. 131, pp. 30-36.
Hermanowski-Vosatka et al., "11B-HSD1 inhibition ameliorates metabolic syndrome and prevents progression of atherosclerosis in mice", Journal of Experimental Medicine, Aug. 15, 2005, vol. 202, No. 4, pp. 517-527, vol. 202, No. 4.
Webster et al., "Discovery and biological evaluation of adamantyl amide 11B-HSD1 inhibitors", Bioorganic & Medicinal Chemistry Letters, 2007, vol. 17, pp. 2838-2843, 17.
Written Opinion 2 in PCTEP2014054604 dated Feb. 10, 2015.
Written Opinion 2 in PCTEP2014054606 dated Feb. 10, 2015.
Written Opinion in PCTEP2014054587 dated Oct. 14, 2014.
He Tielin et al., Handbook of Water Treatment Chemicals, Handbook of Water Treatment Chemicals, May 31, 2000, pp. 116-118; With Translation, First Edition, Chemical Industry Press, CN.
Written Opinion in EP14708586, dated Aug. 2, 2017.

PROLONGED DELIVERY OF CERTAIN FRAGRANCE COMPONENTS FROM PERSONAL CARE COMPOSITIONS

FIELD OF THE INVENTION

The invention concerns personal care compositions which upon application to a human body surface prolong the release of certain highly volatile fragrance components thereby improving aesthetics of these compositions by prolonging the fragrance effect.

BACKGROUND OF THE INVENTION

Perhaps the most significant aesthetic of a personal care product for a consumer is fragrance. It is also important to prolong the life of the scent so the consumers can derive the pleasure from the scent for a longer period of time.

Many techniques have been reported to manipulate timing and impact of fragrance. Delayed generation has been achieved through encapsulation of scent ingredients. For instance, U.S. Pat. No. 5,135,747 (Faryniarz et al.) reports an unscented malodor counteractant deo perfume mixture encapsulated within a semi-permeable wall material and a quicker releasable non-encapsulated fragrance perfume mixture in a cosmetically acceptable vehicle. Slow release has also been achieved through pro-accords. These chemicals slowly break down releasing an odoriferous component as a degradation fragment. Menthol is the most frequent commercially delivered degradation constituent of pro-accords contained in personal care compositions. Illustrative of this technology is U.S. Pat. No. 6,100,233 (Sivik et al.) employing a β-ketoester pro-accord which transforms to chemically release fragranced alcohols such as linalool, dihydromyrcenol and other alcohols.

Steady release technologies have also been reported. Most prominent are a series of disclosures on enduring perfumes. See U.S. Pat. No. 5,833,999; U.S. Pat. No. 5,849,310 and U.S. Pat. No. 6,086,903 all to Trinh et al. describing personal treatment compositions delivering an enduring perfume that provides a lasting olfactory sensation.

Tricyclodecane derivatives, and in some cases tricyclodecane amides, have been described. See for instance Kilburn et al., U.S. Pat. No. 8,053,431B2; WO2004/089415A2 (Novo Nordisk NS); WO2004/089416A2 (Novo Nordisk NS); Narula et al., U.S. Pat. No. 4,985,403; Mathonneau, US 2006057083; WO06/119283 (Hunton & Williams LLP); WO08/054144 (Amorepacific Corporation).

Although technologies are known for delayed release and prolonged perfume generation, there remains a need for alternative commercially feasible technologies, which does not necessitate complicated manufacturing and provides the scent immediately upon application and for prolonged time thereafter.

SUMMARY OF THE INVENTION

A personal care oil and water composition is provided which includes:
(i) from about 0.000001 to about 2% of a fragrance component selected from the group consisting of alpha pinene, beta pinene, hexyl acetate, limonene, (+)-citronellal, dihydromyrcenol, alpha citronellol, beta citronellol, genaniol, lilial, and mixtures thereof;
(ii) from about 0.0001% to about 20% by weight of a tricyclodecane amide of Formula I

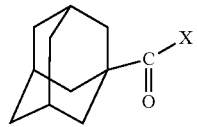

Formula I

Where X is selected from:

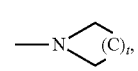

Xa

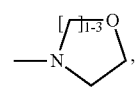

Xb

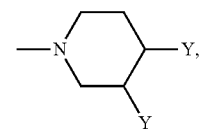

Xc

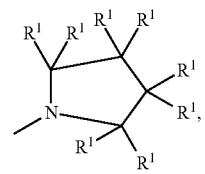

Xd

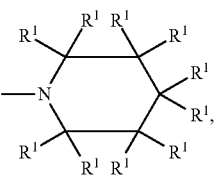

Xe

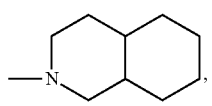

Xf

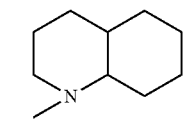

Xg

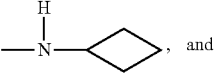

, and

Xh

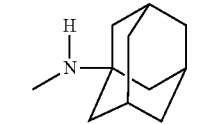

Xi further wherein
t is an integer from 1 to 8; Y is hydrogen,

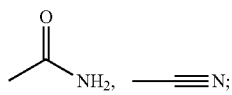

or a halogen
where each $R^1$ is independently a hydrogen or a $C_1$ to 4 alkyl;
(c) a cosmetically acceptable carrier.

The invention also includes a personal care oil and water composition is provided which includes:
(i) from about 0.000001 to about 2% of a fragrance component selected from the group consisting of alpha pinene, beta pinene, hexyl acetate, limonene, (+)-citronellal, and mixtures thereof;
(ii) from about 0.01% to about 30% by weight of a tricyclodecane amide of Formula II

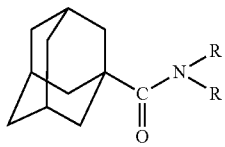

II wherein each R is independently hydrogen, methyl, ethyl or a $C_3$ to $C_{18}$, preferably $C_3$ to $C_{10}$, linear or branched alkyl, cycloalkyl or cycloheteroalkyl group, with the proviso that both R groups are not simultaneously hydrogen; and
(iii) a cosmetically acceptable carrier.

The invention also includes methods of prolonging the scent of selected highly volatile fragrances after application to human body, the inventive compositions.

DETAILED DESCRIPTION OF THE INVENTION

It has been determined as part of the present invention that fragrance components alpha pinene, beta pinene, hexyl acetate, limonene, (+)-citronellal, dihydromyrcenol, alpha citronellol, beta citronellol, geraniol, lilial, and mixtures thereof can have their scent prolonged (volatility suppressed) from a personal care composition containing oil through use of a volatility suppressing agent. This agent has been determined to be tricyclodecane amide. It has been determined that tricyclodecane amides of Formula I have this surprising effect on all of the listed perfumes, and tricyclodecane amides of Formula II have this effect on a subset of perfumes: alpha pinene, beta pinene, hexyl acetate, limonene, (+)-citronellal. Linear (non-cyclic) amides with similar number of carbons do not have this effect. Without wishing to be bound by theory, it is believed that the "cage" structure of tricyclodecane amides leads to specific interaction with certain highly volatile fragrances which reduces their headspace vapor pressure and therefore has a prolonged release of these highly volatile fragrances. It has also been determined that tricyclodecane amides used in the present invention are particularly suitable for personal care compositions because they also suppress sebum production and boost UV-A, UV-B and SPF photoprotection.

By the term personal care composition is meant any product applied to a human body for improving appearance, cleansing, odor control or general aesthetics. Non-limiting examples of personal care compositions include leave-on or rinse-off skin lotions and creams, shampoos, conditioners, shower gels, toilet bars, antiperspirants, deodorants, dental products, shave creams, depilatories, lipsticks, foundations, mascara, sunless tanners and sunscreen lotions. Leave-on compositions are especially preferred since people look forward and expect the scent from the leave-on compositions to last. When the smell disappears too fast, it impacts the positive perception of the product.

It should be noted that in specifying any range of concentration or amount, any particular upper concentration can be associated with any particular lower concentration or amount. "Skin", as used herein, is meant to include skin on the face, neck, chest, back, arms (including underarms), hands, legs, buttocks and scalp. In an especially preferred embodiment, the cosmetic composition of this invention is a leave-on composition for topical application to skin.

An important material of the present invention is tricyclodecane amide of Formula I or of Formula II. Tricyclodecane amides of Formula I are preferred because they have an effect on a larger group of fragrances.

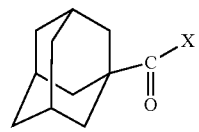

Formula I where X is selected from:

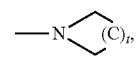

Xa

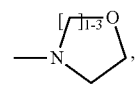

Xb

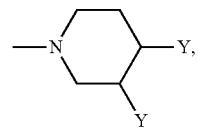

Xc

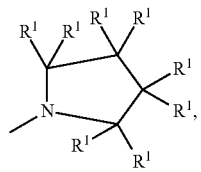

Xd

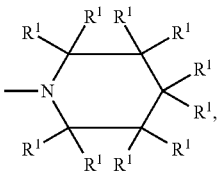

Xe

-continued

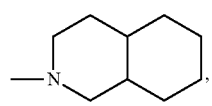 Xf

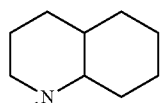 Xg

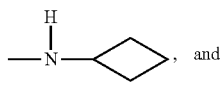 Xh, and

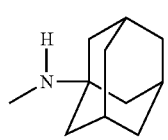 Xi further wherein
t is an integer from 1 to 8; Y is
hydrogen,

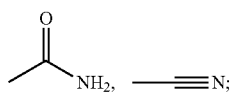

or a halogen
where each $R^1$ is independently a hydrogen or a $C_{1\ to\ 4}$ alkyl.

Preferably, X is selected from groups Xd, Xe, Xf, Xg and, and more preferably Xd and Xe, ideally X is selected from groups Xe and Xd, wherein $R^1$ is hydrogen on all but one carbon and is mono- or di-substituted on that single carbon with methyl or ethyl groups.

Preferred Formula I compounds, wherein X is group Xa, Xb, Xc, Xd, Xe, Xf, Xg, Xh, Xi are:

Methanone, (morphonyl)tricyclo[3.3.1.1$^{3,7}$]dec-1-yl- (C1))
Methanone, (piperidinyl)tricyclo[3.3.1.1$^{3,7}$]dec-1-yl- (C2))
Methanone, (pyrrolidinyl)tricyclo[3.3.1.1$^{3,7}$]dec-1-yl- (C3))
Methanone, (azetidinyl)tricyclo[3.3.1.1$^{3,7}$]dec-1-yl- (C4))
Methanone, (hexahydroazepinyl)tricyclo[3.3.1.1$^{3,7}$]dec-1-yl- (C5))
Methanone, (4-cyano-piperidinyl)tricyclo[3.3.1.1$^{3,7}$]dec-1-yl- (C6)
Methanone, (4-amido-piperidinyl)tricyclo[3.3.1.1$^{3,7}$]dec-1-yl- (C7)
Methanone, (Tricyclo[3.3.1.1$^{3,7}$]decanyl)-N-tricyclo[3.3.1.1$^{3,7}$]dec-1-yl- (C8)
Methanone, (decahydroisoquinolinyl)tricyclo[3.3.1.1$^{3,7}$]dec-1-yl- (C9)
Methanone, (decahydroquinolinyl)tricyclo[3.3.1.1$^{3,7}$]dec-1-yl- (C10)
Methanone, (3,3-dimethyl-1-piperidinyl)tricyclo[3.3.1.1$^{3,7}$]dec-1-yl- (C11)
Methanone, (2-methyl-1-piperidinyl)tricyclo[3.3.1.1$^{3,7}$]dec-1-yl- (C12)
Methanone, (4-methyl-1-piperidinyl)tricyclo[3.3.1.1$^{3,7}$]dec-1-yl- (C13)
Methanone, (3-methyl-1-piperidinyl)tricyclo[3.3.1.1$^{3,7}$]dec-1-yl- (C14)
Methanone, (3,5-dimethyl-1-piperidinyl)tricyclo[3.3.1.1$^{3,7}$]dec-1-yl- (C15)
Methanone, (4-methyl-4-ethy-piperidinyl)tricyclo[3.3.1.1$^{3,7}$]dec-1-yl- (C16)
Methanone, (3,3-diethyl-1-pyrrolidinyl)tricyclo[3.3.1.1$^{3,7}$]dec-1-yl- (C17)

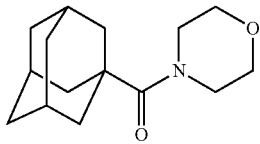 (C1)

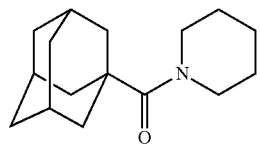 (C2)

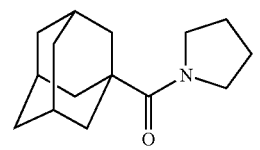 (C3)

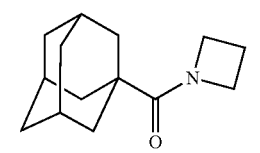 (C4)

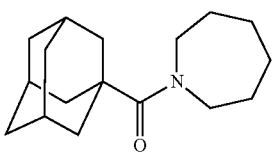 (C5)

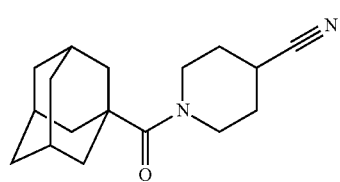 (C6)

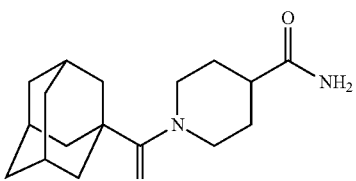 (C7)

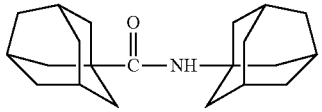 (C8)

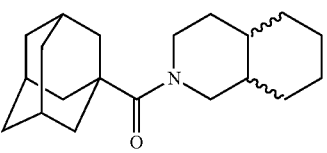 (C9)

-continued

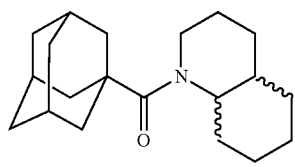
(C10)

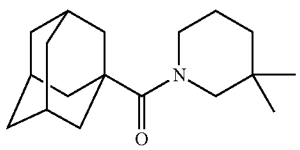
(C11)

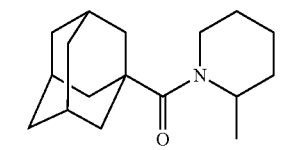
(C12)

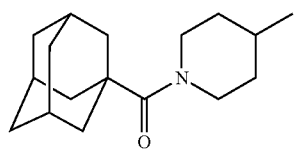
(C13)

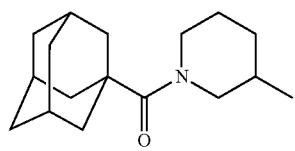
(C14)

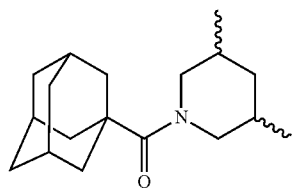
(C15)

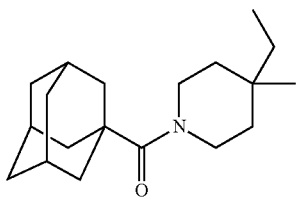
(C16)

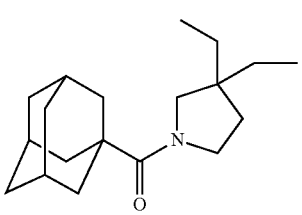
(C17)

More preferred compounds are compounds C9 through 017, and most preferred compounds are C11 through C17.

Tricyclodecane amides of Formula II have the following general structure:

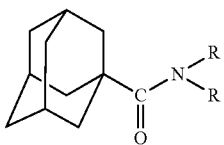
Formula II wherein each R is independently hydrogen, methyl, ethyl or a $C_3$ to $C_{18}$, preferably $C_3$ to $C_{10}$, linear or branched alkyl, cycloalkyl or cycloheteroalkyl group, with the proviso that both R groups are not simultaneously hydrogen; and (iii) a cosmetically acceptable carrier.

Preferably R is a linear or branched alkyl with substitution on tertiary nitrogen.

Examples of formula II preferred structures are:

Methanone, (N,N-diisopropyl)tricyclo[3.3.1.1$^{3,7}$]dec-1-yl- (C18))

Methanone, (3,3-dimethylbutylaminyl)tricyclo[3.3.1.1$^{3,7}$]dec-1-yl- (C19))

Methanone, (2,2-dimethylpropylaminyl)tricyclo[3.3.1.1$^{3,7}$]dec-1-yl- (C20))

Methanone, (1,1-dimethyl-3,3-dimethylbutylaminyl)tricyclo[3.3.1.1$^{3,7}$]dec-1-yl- (C21))

Methanone, (1,3-dimethyl-butylaminyl)tricyclo[3.3.1.1$^{3,7}$]dec-1-yl- (C22)

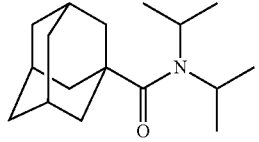
(C18)

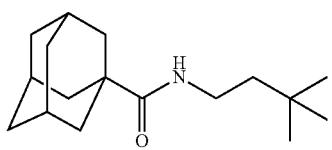
(C19)

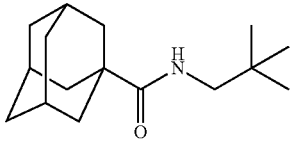
(C20)

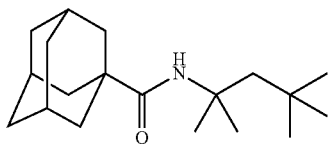
(C21)

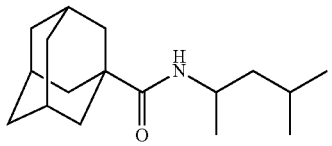
(C22)

Wherein compounds 019, C20, C21 and C22 are more preferred, and compounds C21 and C22 most preferred.

Amounts of the tricyclodecane amides may range from 0.0001 to 20%, preferably from 0.001 to 10%, optimally from 0.01 to 5% by weight of the composition.

Other tricyclodecane amides and other tricyclodecane derivatives may be included in the inventive composition, in addition to the tricyclodecane amides described herein. Likewise, additional perfumes not listed above may also be included.

The fragrance components susceptible of a prolonged effect according to the present invention are alpha pinene, beta pinene, hexyl acetate, limonene, (+)-citronellal, dihydromyrcenol, alpha citronellol, beta citronellol, genaniol, lilial, and mixtures thereof. Amounts of each of these components may each range from 0.000001 to 2%, preferably from 0.00001 to 1.5%, more preferably from 0.0001 to 1%, and optimally from 0.001 to 0.8% by weight of the personal care composition.

Compositions of this invention will also include a cosmetically acceptable carrier. Amounts of the carrier may range from 1 to 99.9%, preferably from 70 to 95%, optimally from 60 to 90% by weight of the composition. Among the useful carriers are water, emollients, fatty acids, fatty alcohols, humectants, thickeners and combinations thereof. The carrier may be aqueous, anhydrous or an emulsion. The inventive compositions need to include oil in order to dissolve tricyclodecane amide and fragrance. Typically, oil is present in an amount of at least twice the amount of tricyclodecane. Preferably the compositions are aqueous, especially water and oil emulsions of the W/O or O/W or triplex W/O/W variety. Water when present may be in amounts ranging from 5 to 95%, preferably from 20 to 70%, optimally from 35 to 60% by weight.

Emollient materials may serve as cosmetically acceptable carriers. These may be in the form of silicone oils, synthetic esters and hydrocarbons. Amounts of the emollients may range anywhere from 0.1 to 95%, preferably between 1 and 50% by weight of the composition.

Silicone oils may be divided into the volatile and nonvolatile variety. The term "volatile" as used herein refers to those materials which have a measurable vapor pressure at ambient temperature. Volatile silicone oils are preferably chosen from cyclic (cyclomethicone) or linear polydimethylsiloxanes containing from 3 to 9, preferably from 4 to 5, silicon atoms.

Nonvolatile silicone oils useful as an emollient material include polyalkyl siloxanes, polyalkylaryl siloxanes and polyether siloxane copolymers. The essentially nonvolatile polyalkyl siloxanes useful herein include, for example, polydimethyl siloxanes with viscosities of from $5 \times 10^{-6}$ to $0.1$ m$^2$/s at 25° C. Among the preferred nonvolatile emollients useful in the present compositions are the polydimethyl siloxanes having viscosities from $1 \times 10^{-6}$ to $4 \times 10^{-4}$ m$^2$/s at 25° C.

Another class of nonvolatile silicones are emulsifying and non-emulsifying silicone elastomers. Representative of this category is Dimethicone/Vinyl Dimethicone Crosspolymer available as Dow Corning 9040, General Electric SFE 839, and Shin-Etsu KSG-18. Silicone waxes such as Silwax WS-L (Dimethicone Copolyol Laurate) may also be useful.

Among the ester emollients are:
1) Alkyl esters of saturated fatty acids having 10 to 24 carbon atoms. Examples thereof include behenyl neopentanoate, isononyl isonanonoate, isopropyl myristate and octyl stearate.
2) Ether-esters such as fatty acid esters of ethoxylated saturated fatty alcohols.
3) Polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. Particularly useful are pentaerythritol, trimethylolpropane and neopentyl glycol esters of $C_1$-$C_{30}$ alcohols.
4) Wax esters such as beeswax, spermaceti wax and tribehenin wax.
5) Sugar ester of fatty acids such as sucrose polybehenate and sucrose polycottonseedate.

Hydrocarbons which are suitable cosmetically acceptable carriers include petrolatum, mineral oil, $C_{11}$-$C_{13}$ isoparaffins, and especially isohexadecane, available commercially as Permethyl 101A from Presperse Inc.

Fatty acids having from 10 to 30 carbon atoms may also be suitable as cosmetically acceptable carriers. Illustrative of this category are pelargonic, lauric, myristic, palmitic, stearic, isostearic, oleic, hydroxystearic and behenic acids.

Fatty alcohols having from 10 to 30 carbon atoms are another useful category of cosmetically acceptable carrier. Illustrative of this category are stearyl alcohol, lauryl alcohol, myristyl alcohol and cetyl alcohol.

Humectants of the polyhydric alcohol-type can be employed as cosmetically acceptable carriers. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. The amount of humectant may range anywhere from 0.5 to 50%, preferably between 1 and 15% by weight of the composition.

Thickeners can be utilized as part of the cosmetically acceptable carrier of compositions according to the present invention. Typical thickeners include crosslinked acrylates (e.g. Carbopol 982®), hydrophobically-modified acrylates (e.g. Carbopol 1382®), cellulosic derivatives and natural gums. Among useful cellulosic derivatives are sodium carboxymethylcellulose, hydroxypropyl methocellulose, hydroxypropyl cellulose, hydroxyethyl cellulose, ethyl cellulose and hydroxymethyl cellulose. Natural gums suitable for the present invention include guar, xanthan, *sclerotium*, carrageenan, pectin and combinations of these gums. Inorganics may also be utilized as thickeners, particularly clays such as bentonites and hectorites, fumed silicas, and silicates such as magnesium aluminum silicate (Veegum®). Amounts of the thickener may range from 0.0001 to 10%, usually from 0.001 to 1%, optimally from 0.01 to 0.5% by weight of the composition.

Personal care compositions of the present invention may be in any form. These forms may include but are not limited to lotions, creams, roll-on formulations, mousses, aerosol and non-aerosol sprays and fabric (e.g. nonwoven textile)-applied formulations.

Surfactants may also be present in compositions of the present invention. Total concentration of the surfactant when present may range from 0.1 to 40%, preferably from 1 to 20%, optimally from 1 to 5% by weight of the composition. The surfactant may be selected from the group consisting of anionic, nonionic, cationic and amphoteric actives. Particularly preferred nonionic surfactants are those with a $C_{10}$-$C_{20}$ fatty alcohol or acid hydrophobe condensed with from 2 to 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di-$C_8$-$C_{20}$ fatty acids; and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfates and sulfonates, alkyl sulfates and sulfonates, alkylbenzene sulfonates, alkyl and dialkyl sulfosuccinates, $C_8$-$C_{20}$ acyl isethionate, $C_8$-$C_{20}$ alkyl ether phosphates, $C_8$-$C_{20}$ sarcosinates and combinations thereof.

Sunscreen actives may also be included in compositions of the present invention. Particularly preferred are such materials as ethylhexyl p-methoxycinnamate (available as Parsol MCX®), Avobenzene (available as Parsol 1789®), octylsalicylate (available as Dermablock OS®), tetraphthalylidene dicamphor sulfonic acid (available as Mexoryl SX®), benzophenone-4 and benzophenone-3 (Oxybenzone) and octocaylene. Inorganic sunscreen actives may be employed such as microfine titanium dioxide, zinc oxide, polyethylene and various other polymers. By the term "microfine" is meant particles of average size ranging from 10 to 200 nm, preferably from about 20 to about 100 nm. Amounts of the sunscreen agents when present may generally range from 0.1 to 30%, preferably from 2 to 20%, optimally from 4 to 10% by weight of the composition.

Preservatives can desirably be incorporated into the cosmetic compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are phenoxyethanol, methyl paraben, propyl paraben, imidazolidinyl urea, sodium dehydroacetate, caprylyl glycol and benzyl alcohol. The preservatives should be selected having regard for the use of the composition and possible incompatibilities between the preservatives and other ingredients in the emulsion. Preservatives are preferably employed in amounts ranging from 0.01% to 2% by weight of the composition.

An especially preferred combination is octocrylene and caprylyl glycol, since caprylyl glycol has been disclosed to enhance UVA and UVB protection.

Compositions of the present invention may include vitamins. Illustrative vitamins are Vitamin A (retinol), Vitamin $B_2$, Vitamin $B_3$ (niacinamide), Vitamin $B_6$, Vitamin C, Vitamin E and Biotin. Derivatives of the vitamins may also be employed. For instance, Vitamin C derivatives include ascorbyl tetraisopalmitate, magnesium ascorbyl phosphate and ascorbyl glycoside. Derivatives of Vitamin E include tocopheryl acetate, tocopheryl palmitate and tocopheryl linoleate. DL-panthenol and derivatives may also be employed. A particularly suitable Vitamin $B_6$ derivative is Pyridoxine Palmitate. Flavanoids may also be useful, particularly glucosyl hesperidin, rutin, and soy isoflavones (including genistein, daidzein, equol, and their glucosyl derivatives) and mixtures thereof. Total amount of vitamins or flavonoids when present may range from 0.0001 to 10%, preferably from 0.01% to 1%, optimally from 0.1 to 0.5% by weight of the composition.

Another type of useful substance can be that of an enzyme such as oxidases, proteases, lipases and combinations. Particularly preferred is superoxide dismutase, commercially available as Biocell SOD from the Brooks Company, USA.

Skin lightening compounds may be included in the compositions of the invention. Illustrative substances are placental extract, lactic acid, niacinamide, arbutin, kojic acid, ferulic acid, resorcinol and derivatives including 4-substituted resorcinols and combinations thereof. Amounts of these agents may range from 0.1 to 10%, preferably from 0.5 to 2% by weight of the composition.

Desquamation promoters may be present. Illustrative are the alpha-hydroxycarboxylic acids and beta-hydroxycarboxylic acids. The term "acid" is meant to include not only the free acid but also salts and $C_1$-$C_{30}$ alkyl or aryl esters thereof and lactones generated from removal of water to form cyclic or linear lactone structures. Representative acids are glycolic, lactic and malic acids. Salicylic acid is representative of the beta-hydroxycarboxylic acids. Amounts of these materials when present may range from 0.01 to 15% by weight of the composition.

A variety of herbal extracts may optionally be included in compositions of this invention. Illustrative are pomegranate, white birch (*Betula Alba*), green tea, chamomile, licorice and extract combinations thereof. The extracts may either be water soluble or water-insoluble carried in a solvent which respectively is hydrophilic or hydrophobic. Water and ethanol are the preferred extract solvents.

Also included may be such materials as lipoic acid, kinetin, retinoxytrimethylsilane (available from Clariant Corp. under the Silcare 1 M-75 trademark), dehydroepiandrosterone (DHEA) and combinations thereof. Ceramides (including Ceramide 1, Ceramide 3, Ceramide 3B, Ceramide 6 and Ceramide 7) as well as pseudoceramides may also be utilized for many compositions of the present invention but may also be excluded. Amounts of these materials may range from 0.000001 to 10%, preferably from 0.0001 to 1% by weight of the composition.

Colorants, opacifiers and abrasives may also be included in compositions of the present invention. Each of these substances may range from 0.05 to 5%, preferably between 0.1 and 3% by weight of the composition.

The compositions of the present invention can also be, optionally, incorporated into a water insoluble substrate for application to the skin such as in the form of a treated wipe.

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

Except in the operating and comparative examples, or where otherwise explicitly indicated, all numbers in this description indicating amounts of material ought to be understood as modified by the word "about".

All documents referred to herein, including all patents, patent applications, and printed publications, are hereby incorporated by reference in their entirety in this disclosure.

The following examples will more fully illustrate the embodiments of this invention. All parts, percentages and proportions referred to herein and in the appended claims are by weight unless otherwise illustrated.

EXAMPLES

Experimental Methods

All reagents and solvents were obtained from commercial sources (Sigma-Aldrich, EMD Chemicals) and used as supplied unless otherwise indicated. Parallel reactions and parallel solvent removal were performed using a Buchi Syncore reactor (Buchi Corporation, New Castle, Del.). Reaction monitoring was performed using thin layer chromatography (TLC). TLC was performed using silica gel 60 F254 plates (EMD Chemicals) and visualizing by UV (254 nm), 4% phosphomolybdic acid (PMA) in ethanol (EtOH), 4% ninhydrin in ethanol and/or using an iodine chamber. Flash chromatography (FC) was performed using a Biotage SP4 system (Biotage LLC, Charlottesville, Va.). High performance liquid chromatography (HPLC) was performed using a Waters 2695 Separations Module equipped with a Waters 2996 Photodiode Array Detector and operated with Empower Pro software (Waters Corp.). Separations were carried out at 1 ml/min on a Restek Pinnacle DB C18 column (5 μm, 4.6×150 mm) maintained at 30° C. Examples for HPLC were prepared by dissolving 1 mg of example in 1 ml mobile phase A:B (1:1) and injecting 5 μL onto the column. The mobile phase consisted of A=0.1% trifluoroacetic acid (TFA) in water and B=0.1% TFA in acetonitrile (ACN) operated using gradient elution from 95:5 A:B to 5:95 A:B (gradient, 25 min) followed by 100% B (isocratic, 5 min). Gas Chromatography (GC) was performed using an Agilent 7890A Gas Chromatograph equipped with an Agilent DB-5HT (15 m×0.32 mm; 0.1μ) column and an FID detector heated at 325° C. Examples were prepared at 25 ppm concentrations in acetone and the injection volume was 1 μL. The air, helium and hydrogen flows were maintained at 400, 25 and 30 ml/min and the separation gradient consisted of 100° C. (isothermal, 1 min), 15° C./min up to 250° C., 250° C. (isothermal, 4 min), 25° C./min up to 300° C., and 300° C. (isothermal, 3 min). Liquid chromatography/mass spectrometry (LC-MS) was performed using a Finnigan Mat LCQ Mass Spectrometer via direct infusion of examples (50 ppm) in methanol and the total ion count monitored using electrospray ionization in the (+) mode (ESI+). 1H and 13C Nuclear magnetic resonance (NMR) spectroscopy was performed using a Eft-60 NMR Spectrometer (Anasazi instruments, Inc.) and processed using WinNuts software (Acorn NMR, Inc.). Melting points were determined using a Meltemp apparatus (Laboratory Devices). Purity was determined by HPLC-UV/Vis and/or GC. All compounds were unequivocally confirmed by LC-MS and/or $^1$H NMR. DCM=Dichloromethane; DIPEA=N, N-Diisopropylethylamine; RT=room temperature; MTBE=Methyl tert-Butyl ether; TFA=Trifluroacetic acid; ACN=acetonitrile; IPA=isopropyl alcohol; FC=flash chromatography.

Examples 1 through 28 as shown demonstrate the synthesis of tricyclodecane amides suitable for use in this invention.

General Procedure

Tricyclo[3.3.1.1$^{3,7}$]decane-1-carbonyl chloride was stirred under nitrogen atmosphere in Dichloromethane and the solution was cooled to 0° C. in an ice bath. A solution of a chosen amine was slowly added to the solution of Tricyclo [3.3.1.1$^{3,7}$]decane-1-carbonyl chloride. Upon completion of addition the reaction mixture was warmed up to room temperature and stirred under N$_2$ overnight. Work up—: water was added to the reaction mixture and was extracted with dichloromethane, washed with 0.1 N HCl, water, sat. NaHCO$_3$ and sat. NaCl solution, dried over Sodium sulfate and evaporated on the rotovap. The solid was purified by a silica gel filtration (silica gel bed, used 15% ethyl acetate in hexane). The filtrate was evaporated on the rotovap, to give pure white crystalline corresponding amides.

Example 1

Synthesis of Methanone, (3,3-dimethyl-1-piperidinyl)tricyclo[3.3.1.1$^{3,7}$]dec-1-yl (Compound C11)

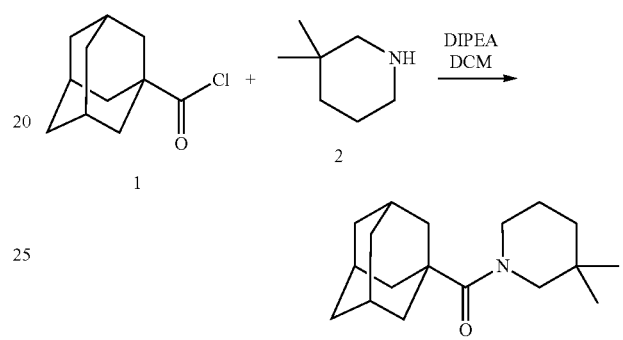

DIPEA (144 μL, 0.8 mmol) was added to a solution of Tricyclo[3.3.1.1$^{3,7}$]decane-1-carbonyl chloride (1) (150 mg, 0.8 mmol) and 3,3-dimethylpiperidine (2) (85 mg, 0.8 mmol) in DCM (2 ml) and the solution stirred at room temperature for 1 hour. At this time, TLC [15:85 EA:hexane, 20 μL aliquot into MTBE:1 N HCl (400 μL:400 μL)] showed the formation of a single product. The reaction mixture was allowed to stir for and additional 16 hours. The solution was diluted with CHCl$_3$ (10 ml), washed with 1N HCl (10 ml), saturated NaHCO$_3$ (10 ml), dried (Na$_2$SO$_4$), filtered and the solvents removed to give crude product as a colorless oil (160 mg). The product was further purified by FC on silica gel using 15:85 EA:hexane to give the desired product as a white solid.

Example 2

Synthesis of Methanone, (decahydroisoquinolinyl) tricyclo[3.3.1.1$^{3,7}$]dec-1-yl- (C9)

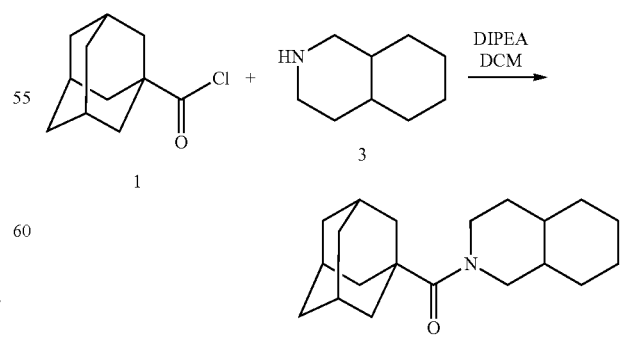

DIPEA (1.93 ml, 11.1 mmol) was added to a solution of Tricyclo[3.3.1.1$^{3,7}$]decane-1-carbonyl chloride (1) (2 g, 10.1 mmol) and decahydroisoquinoline (3) (1.59 ml, 11.1 mmol) in DCM (20 ml) and the solution stirred at room temperature for 4 hours. At this time, TLC [15:85 EA:hexane, 20 µL aliquot into MTBE:1 N HCl (400 µL:400 µL)] showed the formation of a single product. The solution was washed with 0.1N HCl (30 ml), saturated NaHCO$_3$ (30 ml), dried (Na$_2$SO$_4$), filtered and the solvents removed to give crude product which was further purified by FC on silica gel using 15:85 EA:hexane to give the desired product as a white solid.

Example 3

Synthesis of Methanone, (4,4-dimethyl-1-piperidinyl)tricyclo[3.3.1.1$^{3,7}$]dec-1-yl

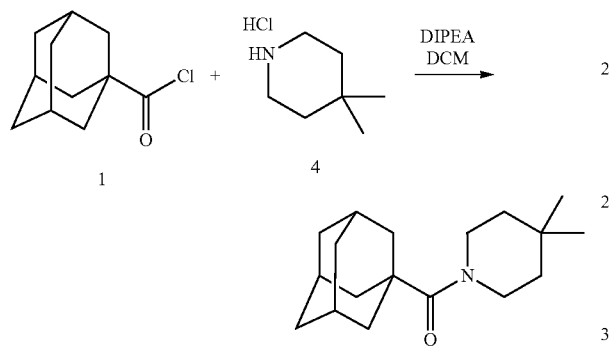

DIPEA (1.93 ml, 11.1 mmol) was added to a solution of Tricyclo[3.3.1.1$^{3,7}$]decane-1-carbonyl chloride (1) (1 g, 5.5 mmol) and 4,4-dimethylpiperidine hydrochloride (4) (828 mg, 5.5 mmol) in DCM (10 ml) and the solution stirred at room temperature for 4 hours. At this time, TLC [15:85 EA:hexane, 20 µL aliquot into MTBE:1 N HCl (400 µL:400 µL)] showed the formation of a single chemical. The solution was washed with 0.1N HCl (30 ml), saturated NaHCO$_3$ (30 ml), dried (Na$_2$SO$_4$), filtered and the solvents removed to give crude product which was further purified by FC on silica gel using 15:85 EA:hexane to give the desired product as a crystalline white solid.

Example 4

Synthesis of Methanone, (cyclopentylaminyl)tricyclo[3.3.1.1$^{3,7}$]dec-1-yl

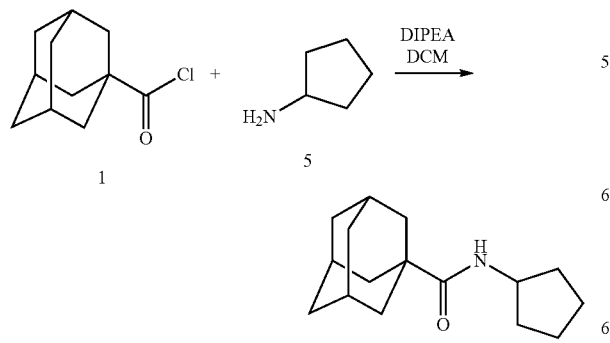

DIPEA (1.93 ml, 11.1 mmol) was added to a solution of Tricyclo[3.3.1.1$^{3,7}$]decane-1-carbonyl chloride (1) (2 g, 10.1 mmol) and cyclopentylamine (5) (1.09 ml, 11.1 mmol) in DCM (20 ml) and the solution stirred at room temperature for 4 hours. At this time, TLC [15:85 EA:hexane, 20 µL aliquot into MTBE:1 N HCl (400 µL:400 µL)] showed the formation of a single product. The solution was washed with 0.1N HCl (30 ml), saturated NaHCO$_3$ (30 ml), dried (Na$_2$SO$_4$), filtered and the solvents removed to give crude product which was further purified via crystallization from 15% EA in hexanes to give the desired product as a white solid.

Example 5

Synthesis of Methanone, (4-methyl-1-piperidinyl)tricyclo[3.3.1.1$^{3,7}$]dec-1-yl (Compound C13)

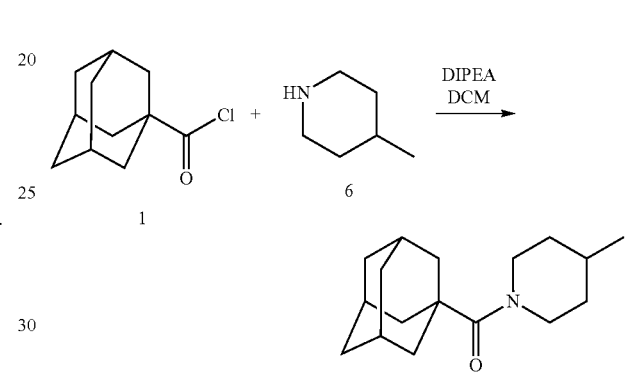

DIPEA (1.93 ml, 11.1 mmol) was added to a solution of Tricyclo[3.3.1.1$^{3,7}$]decane-1-carbonyl chloride (1) (1 g, 5.5 mmol) and 4-methylpiperidine (6) (1.27 ml, 11.1 mmol) in DCM (20 ml) and the solution stirred at room temperature for 4 hours. At this time, TLC [15:85 EA:hexane, 20 µL aliquot into MTBE:1 N HCl (400 µL:400 µL)] showed the formation of a single product. The solution was washed with 0.1N HCl (30 ml), saturated NaHCO$_3$ (30 ml), dried (Na$_2$SO$_4$), filtered and the solvents removed to give crude product which was further purified by FC on silica gel using 15:85 EA:hexane to give the desired product as a white solid.

Example 6

Synthesis of Methanone, (3-methyl-1-piperidinyl)tricyclo[3.3.1.1$^{3,7}$]dec-1-yl (Compound C14)

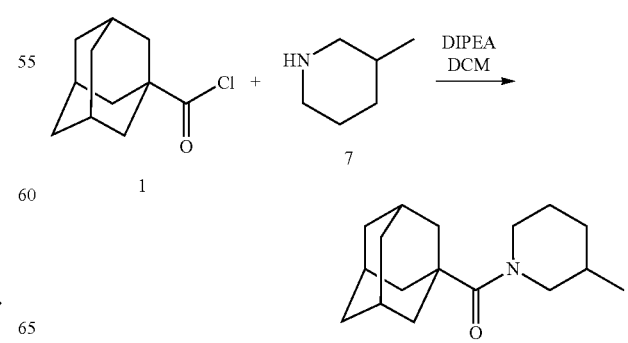

DIPEA (1.93 ml, 11.1 mmol) was added to a solution of Tricyclo[3.3.1.1$^{3,7}$]decane-1-carbonyl chloride (1) (1 g, 5.5 mmol) and 3-methylpiperidine (7) (1.31 ml, 11.1 mmol) in DCM (20 ml) and the solution stirred at room temperature for 4 hours. At this time, TLC[15:85 EA:hexane, 20 µL aliquot into MTBE:1 N HCl (400 µL:400 µL)] showed the formation of a single product and some SM remaining. The solution was washed with 0.1N HCl (30 ml), saturated NaHCO$_3$ (30 ml), dried (Na$_2$SO$_4$), filtered and the solvents removed to give crude product which was further purified by FC on silica gel using 15:85 EA:hexane to give the desired product as a white solid.

Example 7

Synthesis of Methanone, (4-amido-piperidinyl)tricyclo[3.3.1.1$^{3,7}$]dec-1-yl- (Compound C7)

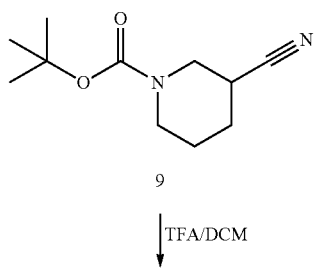

4-Piperidinecarboxamide (8) (71 mg, 0.6 mmol) was dissolved in ACN:CHCl$_3$ (3 ml, 1:1) solution by gentle warming. DIPEA (96 µL, 0.6 mmol) was added, followed by Tricyclo[3.3.1.1$^{3,7}$]decane-1-carbonyl chloride (1) (100 mg, 0.5 mmol) and the solution stirred at room temperature for 20 hours. At this time, TLC [7% MeOH in CHCl$_3$, 20 µL aliquot into MTBE:1 N HCl (400 µL:400 µL)] showed the formation of a single product. The solution was diluted with 15% IPA in CHCl$_3$ (8 ml), washed with 0.1 N HCl (8 ml), saturated NaHCO$_3$ (8 ml), dried (Na$_2$SO$_4$), filtered and the solvents removed to give crude product which was further purified by FC on silica gel using 7% MeOH in CHCl$_3$ to give product as a white solid.

Example 8

Synthesis of Methanone, (3-cyano-piperidinyl)tricyclo[3.3.1.1$^{3,7}$]dec-1-yl-

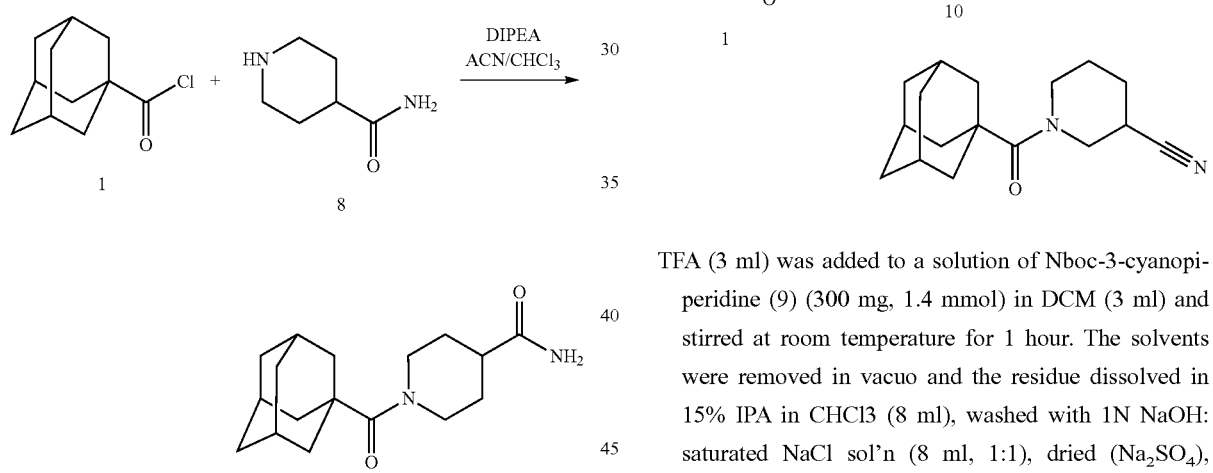

TFA (3 ml) was added to a solution of Nboc-3-cyanopiperidine (9) (300 mg, 1.4 mmol) in DCM (3 ml) and stirred at room temperature for 1 hour. The solvents were removed in vacuo and the residue dissolved in 15% IPA in CHCl3 (8 ml), washed with 1N NaOH: saturated NaCl sol'n (8 ml, 1:1), dried (Na$_2$SO$_4$), filtered and the solvents removed to give 3-cyanopiperidine (10) (141 mg, 90% yield) which was used crude for the next step. Tricyclo[3.3.1.1$^{3,7}$]decane-1-carbonyl chloride (1) (100 mg, 0.5 mmol) was added to a solution of 3-cyanopiperidine (10) (61 mg, 0.6 mmol) and DIPEA (96 µL, 0.6 mmol) in CHCl$_3$ (1 ml) and the solution stirred for 16 hours. At this time, TLC [40:60 EA:hexane, 20 µL aliquot into MTBE:1 N HCl (400 µL:400 µL)] showed the formation of a major product. The solution was diluted with CHCl$_3$ (8 ml), washed with 0.1N HCl (8 ml), saturated NaHCO$_3$ (8 ml), dried (Na$_2$SO$_4$), filtered and the solvents removed to give crude product which was further purified by FC on silica gel using 40:60 EA:hexane to give product as a white solid.

Example 9

Synthesis of Methanone, (4-cyano-piperidinyl)tricyclo[3.3.1.1³,⁷]dec-1-yl (Compound C6)

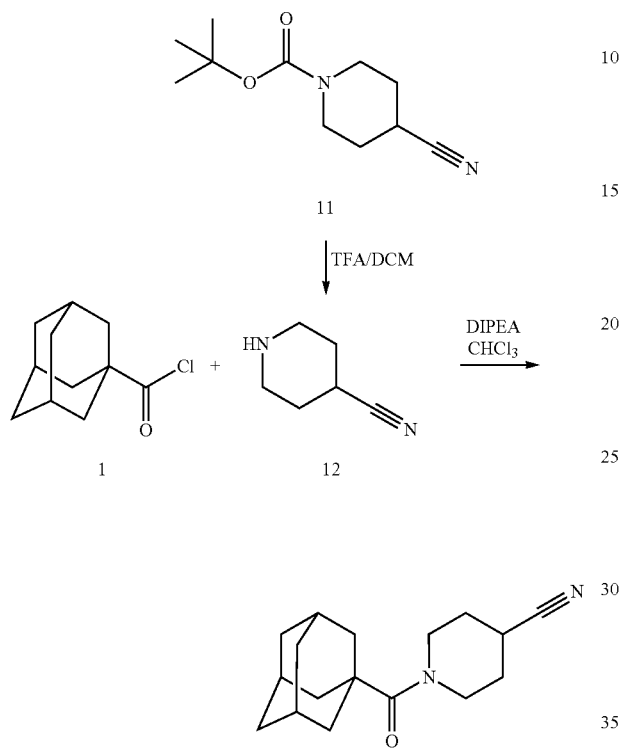

TFA (3 ml) was added to a solution of Nboc-4-cyanopiperidine (11) (300 mg, 1.4 mmol) in DCM (3 ml) and stirred at room temperature for 1 hour. The solvents were removed in vacuo and the residue dissolved in 15% IPA in CHCl3 (8 ml), washed with 1N NaOH: saturated NaCl sol'n (8 ml, 1:1), dried ($Na_2SO_4$), filtered and the solvents removed to give 4-cyanopiperidine (12) (141 mg, 90% yield) which was used crude for the next step. Tricyclo[3.3.1.1³,⁷]decane-1-carbonyl chloride (1) (230 mg, 1.2 mmol) was added to a solution of 4-cyanopiperidine (12) (140 mg, 1.3 mmol) and DIPEA (222 µL, 1.3 mmol) in $CHCl_3$ (2 ml) and the solution stirred at room temperature for 16 hours. At this time, TLC [40:60 EA:hexane, 20 µL aliquot into MTBE:1 N HCl (400 µL:400 µL)] showed the formation of a major product. The solution was diluted with $CHCl_3$ (8 ml), washed with 0.1N HCl (8 ml), saturated $NaHCO_3$ (8 ml), dried ($Na_2SO_4$), filtered and the solvents removed to give crude product which was further purified by FC on silica gel using 40:60 EA:hexane to give product as a white solid.

Example 10

Synthesis of Methanone, (1,1-dimethyl-3,3-dimethylbutylaminyl)tricyclo[3.3.1.1³,⁷]dec-1-yl- (Compound C21)

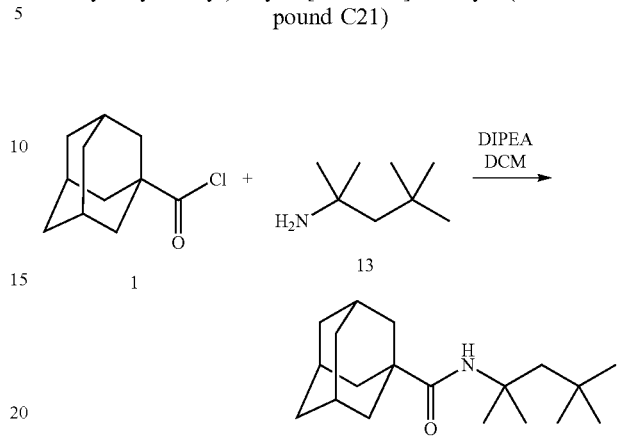

Tricyclo[3.3.1.1³,⁷]decane-1-carbonyl chloride (1) (300 mg, 1.5 mmol) was stirred under nitrogen atmosphere in DCM (3 mL) and the solution was cooled to 0° C. in an ice bath. DIPEA (300 µL, 1.7 mmol) and 1,1-dimethyl-3,3-dimethylbutylamine (13) (271 µL, 1.7 mmol) were mixed and added to the Tricyclo[3.3.1.13,7]decane-1-carbonyl chloride solution slowly. The reaction mixture was allowed to warm up to room temperature and stirred under nitrogen for 16 hours. The reaction was diluted with DCM and washed sequentially with 0.1 N HCl, water, saturated $NaHCO_3$, saturated NaCl, dried ($Na_2SO_4$), filtered and the solvents removed to give crude product which was purified by FC on silica gel using 15% EA in hexane to give product as a white solid.

Example 11

Synthesis of Methanone, (3,3-dimethylbutylaminyl)tricyclo[3.3.1.1³,⁷]dec-1-yl- (Compound 019)

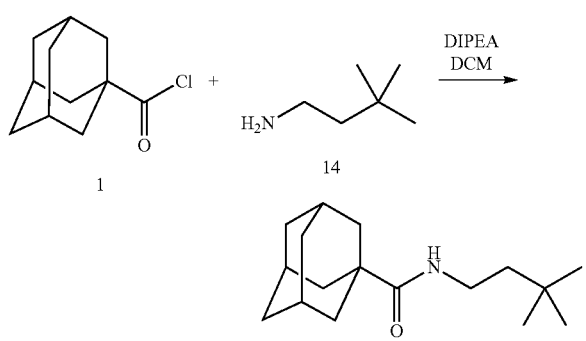

Tricyclo[3.3.1.1³,⁷]decane-1-carbonyl chloride (1) (300 mg, 1.5 mmol) was stirred under nitrogen atmosphere in DCM (3 mL) and the solution to 0° C. in an ice bath. DIPEA (300 µL, 1.7 mmol) and 3,3-dimethylbutylamine (14) (228 µL, 1.7 mmol) were mixed and added to the Tricyclo[3.3.1.13,7]decane-1-carbonyl chloride solution slowly. The reaction mixture was allowed to warm up to room temperature and stirred under nitrogen for 16 hours. The reaction was diluted with DCM and washed sequentially with 0.1 N HCl, water, saturated NaHCO₃, saturated NaCl, dried (Na₂SO₄), filtered and the solvents removed to give crude product which was purified by FC on silica gel using 15% EA in hexane to give product as a white solid.

Example 12

Synthesis of Methanone, (decahydroquinolinyl) tricyclo[3.3.1.1$^{3,7}$]dec-1-yl- (Compound C10)

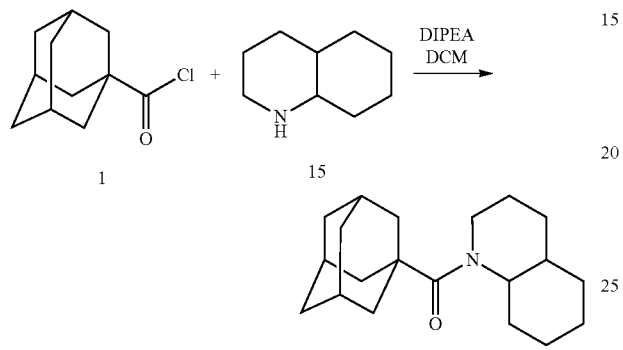

Tricyclo[3.3.1.1$^{3,7}$]decane-1-carbonyl chloride (1) (40.0 g, 0.200 moles) was stirred under nitrogen atmosphere in DCM (340 mL, 1.2 M) and the solution cooled to 0° C. in an ice bath. DIPEA (27.3 g, 18.44 mL, 0.210 moles) and decahydroquinoline (15) (28.35 g, 30.28 mL, 0.210 moles) were mixed and added to the Tricyclo[3.3.1.13,7]decane-1-carbonyl chloride solution slowly. The reaction mixture was allowed to warm up to room temperature and stirred under nitrogen for 16 hours. The reaction was diluted with DCM and washed sequentially with 0.1 N HCl, water, saturated NaHCO₃, saturated NaCl, dried (Na₂SO₄), filtered and the solvents removed to give crude product which was purified on silica gel (filtration through a 3" bed of silica gel) using 15:85 EA:hexane to give product as a white crystalline solid.

Example 13

Synthesis of Methanone, (TRANS-decahydroquinolinyl)tricyclo[3.3.1.1$^{3,7}$]dec-1-yl-

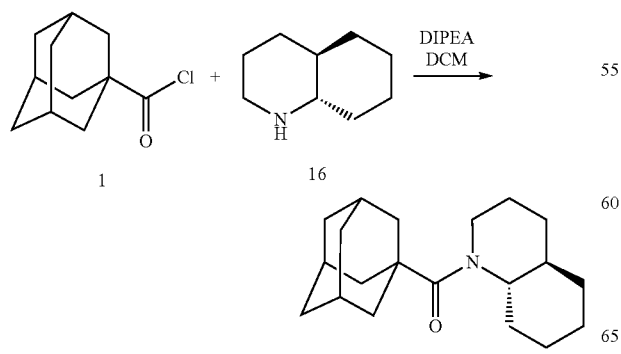

Tricyclo[3.3.1.1$^{3,7}$]decane-1-carbonyl chloride (1) (200 mg, 1 mmoles) was added to a solution of trans-decahydroquinoline (16) (154 mg, 1.1 mmoles) and DIPEA (193 µL, 1.1 mmoles) in CHCl₃ (2 ml) and the solution stirred at room temperature for 16 hours. The reaction mixture was diluted with CHCl₃ (8 ml) and washed sequentially with 0.1 N HCl, saturated NaHCO₃, dried (Na₂SO₄), filtered and the solvents removed to give crude product which was purified by FC on silica gel using 7% EA in hexane to give product as a white solid.

Example 14

Methanone, (azetidinyl)tricyclo[3.3.1.1$^{3,7}$]dec-1-yl- (Compound C4)

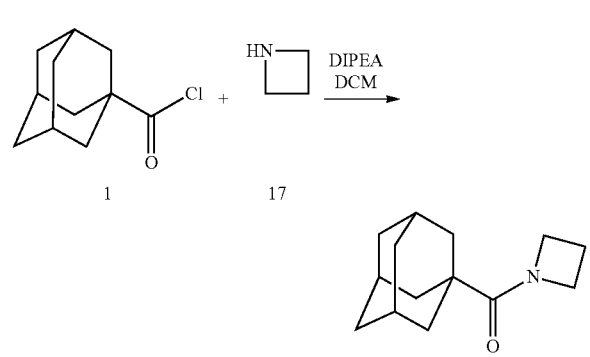

Tricyclo[3.3.1.1$^{3,7}$]decane-1-carbonyl chloride (1) (300 mg, 1.6 mmol) was stirred under nitrogen atmosphere in DCM (3 mL) and the solution cooled to 0° C. in an ice bath. DIPEA (540 µL, 3.1 mmol) and azetidine hydrochloride (17) (148 mg, 1.6 mmol) were mixed and added to the Tricyclo[3.3.1.13,7]decane-1-carbonyl chloride solution slowly. The reaction mixture was allowed to warm up to room temperature and stirred under nitrogen for 16 hours. EA:water (10 ml; 1:1) was added, the organic layer separated and the aqueous layer washed with EA (5 ml). The combined organic layers were sequentially washed with 0.1 N HCl, water, saturated NaHCO₃, saturated NaCl, dried (Na₂SO₄), filtered and the solvents removed to give crude product which was purified by FC on silica gel using 15-25% EA in hexane to give product as a white solid.

Example 15

Synthesis of Methanone, (pyrrolidinyl)tricyclo[3.3.1.1$^{3,7}$]dec-1-yl-

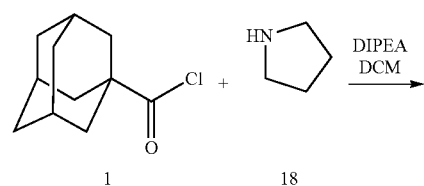

-continued

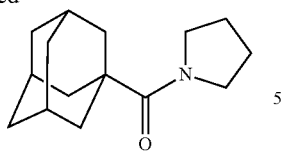

Tricyclo[3.3.1.1$^{3,7}$]decane-1-carbonyl chloride (1) (300 mg, 1.6 mmol) was stirred under nitrogen atmosphere in DCM (3 mL) and the solution cooled to 0° C. in an ice bath. DIPEA (300 µL, 1.7 mmol) and pyrrolidine (18) (131 µL, 1.7 mmol) were mixed and added to the Tricyclo[3.3.1.13,7]decane-1-carbonyl chloride solution slowly. The reaction mixture was allowed to warm up to room temperature and stirred under nitrogen for 16 hours. The obtained precipitate was filtered and washed with 1 N HCl, water and dried under high vacuum. The crude product was purified over a silica gel bed to give product as a white solid (334 mg, 95%).

Example 16

Synthesis of Methanone, (hexahydroazepinyl)tricyclo[3.3.1.1$^{3,7}$]dec-1-yl- (Compound C5)

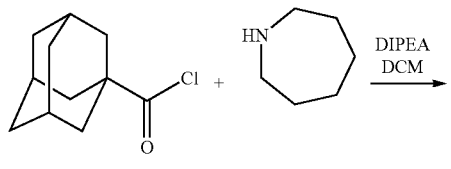

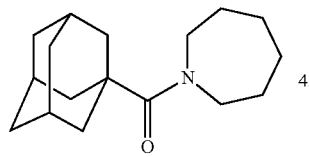

Tricyclo[3.3.1.1$^{3,7}$]decane-1-carbonyl chloride (1) (300 mg, 1.6 mmol) was stirred under nitrogen atmosphere in DCM (3 mL) and the solution cooled to 0° C. in an ice bath. DIPEA (300 µL, 1.7 mmol) and azepane (19) 192 µL, 1.7 mmol) were mixed and added to the Tricyclo[3.3.1.13,7]decane-1-carbonyl chloride solution slowly. The reaction mixture was allowed to warm up to room temperature and stirred under nitrogen for 16 hours. EA was added and the organic layer washed with 1N HCl, saturated NaCl, dried (Na$_2$SO$_4$), filtered and the solvents removed to give crude product which was purified by FC on silica gel using 15:85 EA:hexane to give product as a white solid.

Example 17

Synthesis of Methanone, (2-methyl-1-piperidinyl)tricyclo[3.3.1.1$^{3,7}$]dec-1-yl- (Compound C12)

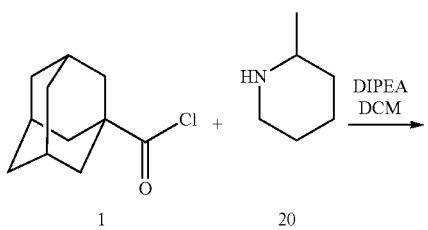

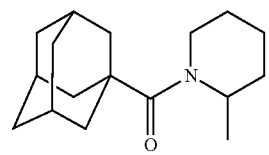

Tricyclo[3.3.1.1$^{3,7}$]decane-1-carbonyl chloride (1) (300 mg, 1.6 mmol) was stirred under nitrogen atmosphere in DCM (3 mL) and the solution cooled to 0° C. in an ice bath. DIPEA (300 µL, 1.7 mmol) and 2-methylpiperidine (20) (216 mg, 1.7 mmol) were mixed and added to the Tricyclo[3.3.1.13,7]decane-1-carbonyl chloride solution slowly. The reaction mixture was allowed to warm up to room temperature and stirred under nitrogen for 16 hours. EA was added and the organic layer washed with 1N HCl, saturated NaCl, dried (Na$_2$SO$_4$), filtered and the solvents removed to give crude product which was purified by FC on silica gel using 15:85 EA:hexane to give product as a white solid.

Example 18

Synthesis of Methanone, (3,5-dimethyl-1-piperidinyl)tricyclo[3.3.1.1$^{3,7}$]dec-1-yl- (Compound C15)

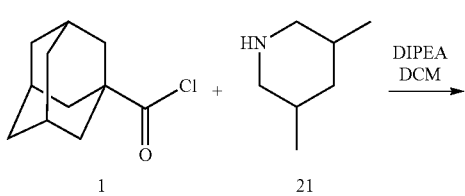

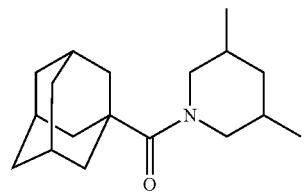

Tricyclo[3.3.1.1$^{3,7}$]decane-1-carbonyl chloride (1) (300 mg, 1.6 mmol) was stirred under nitrogen atmosphere in DCM (3 mL) and the solution cooled to 0° C. in an ice bath. DIPEA (300 µL, 1.7 mmol) and 3,5-dimethylpiperidine (21) (226 µL, 1.7 mmol) were mixed and added to the Tricyclo[3.3.1.1$^{3,7}$]decane-1-carbonyl chloride solution slowly. The reaction mixture was allowed to warm up to room temperature and stirred under nitrogen for 16 hours. Water was added, the organic layer separated and the aqueous layer washed with DCM (5 ml). The combined organic layers were sequentially washed with 0.1 N HCl, water, saturated NaHCO$_3$, saturated NaCl, dried (Na$_2$SO$_4$), filtered and the solvents removed to give crude product which was purified by FC on silica gel using 12:88 EA:hexane to give product as a white solid.

Example 19

Synthesis of Methanone, (4-methyl-4-ethy-piperidinyl)tricyclo[3.3.1.1$^{3,7}$]dec-1-yl- (Compound C16)

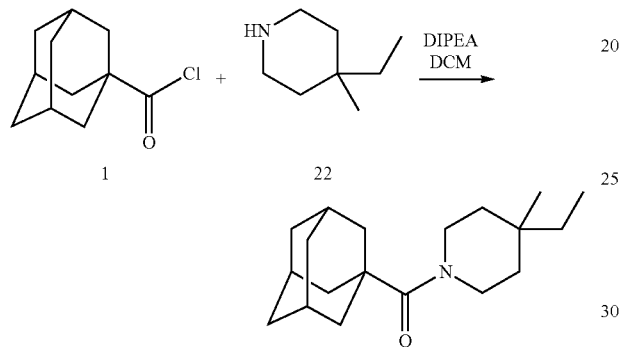

Tricyclo[3.3.1.1$^{3,7}$]decane-1-carbonyl chloride (1) (300 mg, 1.6 mmol) was stirred under nitrogen atmosphere in DCM (3 mL) and the solution cooled to 0° C. in an ice bath. DIPEA (300 µL, 1.7 mmol) and 4-ethyl-4-methylpiperidine (22) (216 mg, 1.7 mmol) were mixed and added to the Tricyclo[3.3.1.1$^{3,7}$]decane-1-carbonyl chloride solution slowly. The reaction mixture was allowed to warm up to room temperature and stirred under nitrogen for 16 hours. Water was added, the organic layer separated and the aqueous layer washed with DCM (5 ml). The combined organic layers were sequentially washed with 0.1 N HCl, water, saturated NaHCO$_3$, saturated NaCl, dried (Na$_2$SO$_4$), filtered and the solvents removed to give crude product which was purified by FC on silica gel using 12:88 EA:hexane to give product as a white solid.

Example 20

Synthesis of Methanone, (3,3-diethyl-pyrrolidinyl) tricyclo[3.3.1.1$^{3,7}$]dec-1-yl- (Compound C171

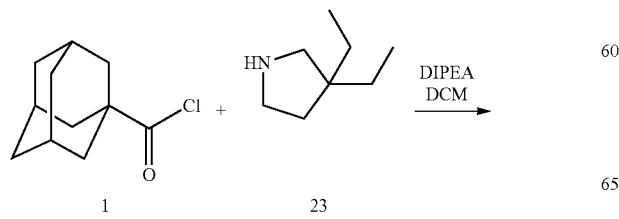

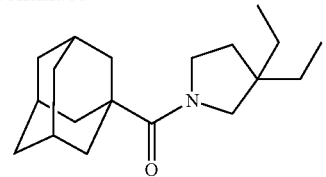

Tricyclo[3.3.1.1$^{3,7}$]decane-1-carbonyl chloride (1) (300 mg, 1.6 mmol) was stirred under nitrogen atmosphere in DCM (3 mL) and the solution cooled to 0° C. in an ice bath. DIPEA (300 µL, 1.7 mmol) and 3,3-diethylpyrrolidine (23) (216 mg, 1.7 mmol) were mixed and added to the Tricyclo[3.3.1.1$^{3,7}$]decane-1-carbonyl chloride solution slowly. The reaction mixture was allowed to warm up to room temperature and stirred under nitrogen for 16 hours. EA was added and the organic layer washed with 1N HCl, saturated NaCl, dried (Na$_2$SO$_4$), filtered and the solvents removed to give crude product which was purified by FC on silica gel using 15:85 EA:hexane to give product as a white solid.

Example 21

Synthesis of Methanone, (cyclobutylaminyl)tricyclo [3.3.1.1$^{3,7}$]dec-1-yl-

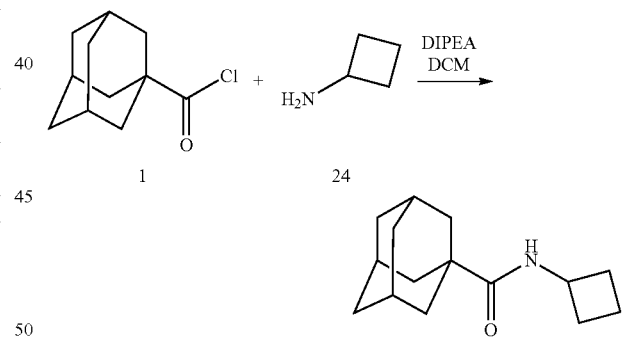

Tricyclo[3.3.1.1$^{3,7}$]decane-1-carbonyl chloride (1) (300 mg, 1.6 mmol) was stirred under nitrogen atmosphere in DCM (3 mL) and the solution cooled to 0° C. in an ice bath. DIPEA (300 µL, 1.7 mmol) and cyclobutylamine (24) (150 µL, 1.7 mmol) were mixed and added to the Tricyclo[3.3.1.13,7]decane-1-carbonyl chloride solution slowly. The reaction mixture was allowed to warm up to room temperature and stirred under nitrogen for 16 hours. The obtained precipitate was filtered and washed with 1 N HCl, water and dried under high vacuum. The crude product was purified over a silica gel bed to give product as a white solid.

Example 22

Synthesis of Methanone, (2,2-dimethylpropylaminyl)tricyclo[3.3.1.1$^{3,7}$]dec-1-yl- (Compound C201)

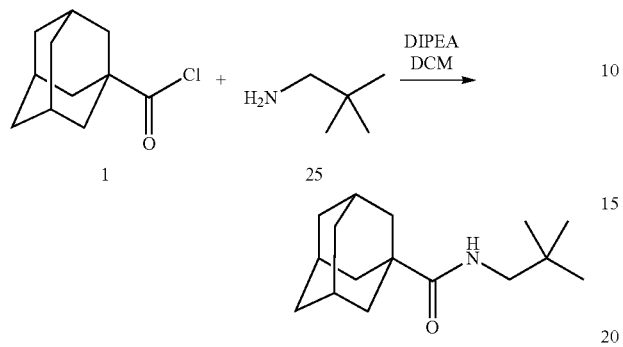

Tricyclo[3.3.1.1$^{3,7}$]decane-1-carbonyl chloride (1) (300 mg, 1.6 mmol) was stirred under nitrogen atmosphere in DCM (3 mL) and the solution cooled to 0° C. in an ice bath. DIPEA (300 µL, 1.7 mmol) and 2,2-dimethylpropylamine (25) (150 µL, 1.7 mmol) were mixed and added to the Tricyclo[3.3.1.1$^{3,7}$]decane-1-carbonyl chloride solution slowly. The reaction mixture was allowed to warm up to room temperature and stirred under nitrogen for 16 hours. The obtained precipitate was filtered and washed with water and dried under high vacuum. The crude product was purified over a silica gel bed to give product as a white solid.

Example 23

Synthesis of Methanone, (N,N-diisopropyl)tricyclo[3.3.1.1$^{3,7}$]dec-1-yl- (Compound C18)

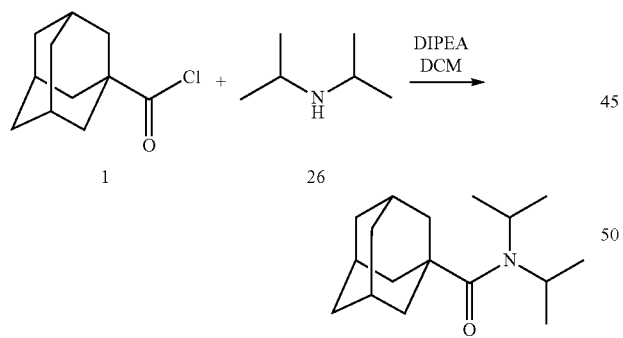

Tricyclo[3.3.1.1$^{3,7}$]decane-1-carbonyl chloride (1) (300 mg, 1.6 mmol) was stirred under nitrogen atmosphere in DCM (3 mL) and the solution cooled to 0° C. in an ice bath. DIPEA (300 µL, 1.7 mmol) and diisopropylamine (26) (232 µL, 1.7 mmol) were mixed and added to the Tricyclo[3.3.1.13,7]decane-1-carbonyl chlorides solution slowly. The reaction mixture was allowed to warm up to room temperature and stirred under nitrogen for 16 hours. The obtained precipitate was filtered and washed with EA. The filtrates were combined and sequentially washed with 0.1 N HCl, water, saturated NaHCO$_3$, saturated NaCl, dried (Na$_2$SO$_4$), filtered and the solvents removed to give crude product which was purified by FC on silica gel using 20:80 EA:hexane to give product as a white solid.

Example 24

Synthesis of Methanone, (1,3-dimethyl-butylaminyl)tricyclo[3.3.1.1$^{3,7}$]dec-1-yl- (Compound C22)

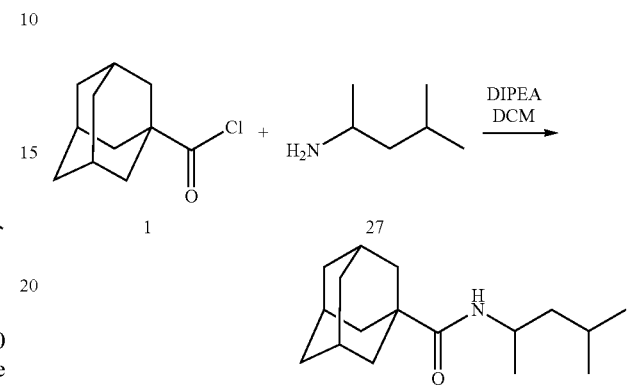

Tricyclo[3.3.1.1$^{3,7}$]decane-1-carbonyl chloride (1) (300 mg, 1.6 mmol) was stirred under nitrogen atmosphere in DCM (4 mL) and the solution cooled to 0° C. in an ice bath. DIPEA (300 µL, 1.7 mmol) and 1,3-dimethylbutylamine (27) (239 µL, 1.7 mmol) were mixed and added to the Tricyclo[3.3.1.1$^{3,7}$]decane-1-carbonyl chloride solution slowly. The reaction mixture was allowed to warm up to room temperature and stirred under nitrogen for 16 hours. The obtained precipitate was filtered and washed with water and dried under high vacuum. The crude product was purified over a silica gel bed to give product as a white solid.

Example 25

Synthesis of Methanone, (Tricyclo[3.3.1.1$^{3,7}$]decanyl)-N-tricyclo[3.3.1.1$^{3,7}$]dec-1-yl- (Compound C8)

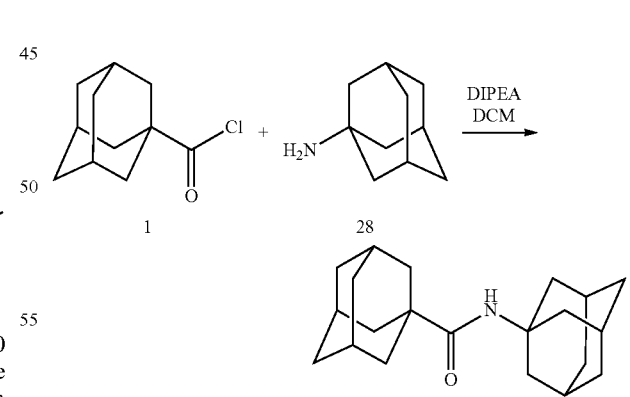

Tricyclo[3.3.1.1$^{3,7}$]decane-1-carbonyl chloride (1) (300 mg, 1.6 mmol) was stirred under nitrogen atmosphere in DCM (3 mL) and the solution cooled to 0° C. in an ice bath. DIPEA (300 µL, 1.7 mmol) and Tricyclo[3.3.1.1$^{3,7}$]decan-1-amine (28) (257 mg, 1.7 mmol) were mixed and added to the Tricyclo[3.3.1.13,7]decane-1-carbonyl chloride solution slowly. The reaction mixture was allowed to warm up to room temperature and stirred under nitrogen for 16 hours. The obtained precipitate was filtered and washed with water and dried under high vacuum. The crude product was purified by FC on silica gel using 15:85 EA:hexane containing 0.1% DIPEA, followed by elution with CHCl₃ to give product as a white solid.

Example 26

Methanone, (3-aminotetrahydrofuranyl)tricyclo[3.3.1.1³,⁷]dec-1-yl-

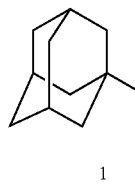 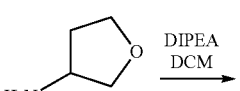

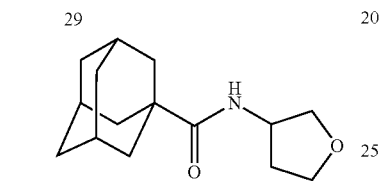

DIPEA (1.93 ml, 11.1 mmol) was added to a solution of Tricyclo[3.3.1.1³,⁷]decane-1-carbonyl chloride (1) (2 g, 10.1 mmol) and 3-aminotetrahydrofuran; (29)(1.0 ml, 11 mmol) in DCM (20 ml) and the solution stirred at room temperature for 4 hours. The solution was washed with 0.1N HCl (30 ml), saturated NaHCO₃ (30 ml), dried (Na₂SO₄), filtered and the solvents removed to give crude product which was further purified via crystallization from 15% EA in hexanes to give as a white solid.

Example 27

Methanone, (morphonyl)tricyclo[3.3.1.1³,⁷]dec-1-yl- (Compound C1)

 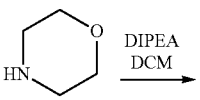

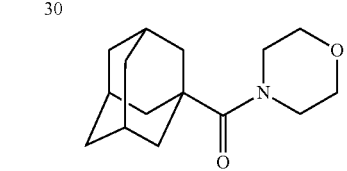

DIPEA (1.93 ml, 11.1 mmol) was added to a solution of Tricyclo[3.3.1.1³,⁷]decane-1-carbonyl chloride (1) (2 g, 10.1 mmol) and morpholine; (30)(1.1 g) in DCM (20 ml) and the solution stirred at room temperature for 4 hours. The solution was washed with 0.1N HCl (30 ml), saturated NaHCO₃ (30 ml), dried (Na₂SO₄), filtered and the solvents removed to give crude product which was further purified via crystallization from 15% EA in hexanes to give as a white solid.

Example 28

Methanone, (piperidinyl)tricyclo[3.3.1.1³,⁷]dec-1-yl- (Compound C2)

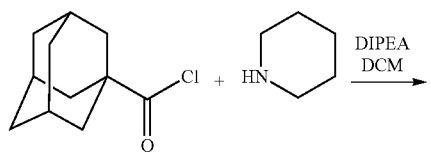

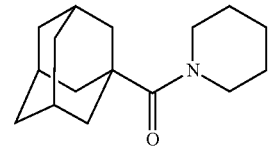

DIPEA (1.93 ml, 11.1 mmol) was added to a solution of Tricyclo[3.3.1.1³,⁷]decane-1-carbonyl chloride (1) (2.1 g, 10.1 mmol) and piperidine (31) (1.1 g) in DCM (20 ml) and the solution stirred at room temperature for 4 hours. At this time, TLC 15:85 EA [ethylacetate:hexane, 20 μL aliquot into MTBE:1 N HCl (400 μL:400 μL)] showed the formation of a single product and some starting material. The solution was washed with 0.1N HCl (30 ml), saturated NaHCO₃ (30 ml), dried (Na₂SO₄), filtered and the solvents removed to give crude product which was further purified via crystallization from 15% EA in hexanes to give as a white solid.

Example 29

A representative personal care composition of the present invention in the form of a cosmetic lotion is outlined under Table I.

TABLE I

| INGREDIENT | WEIGHT % |
|---|---|
| PHASE A | |
| Water | Balance |
| Disodium EDTA | 0.05 |
| Methyl Paraben | 0.15 |
| Magnesium Aluminum Silicate | 0.60 |
| Triethanolamine | 1.20 |
| Methanone, (3-methyl-1-piperidinyl)tricyclo[3.3.1.1³,⁷]dec-1-yl-(Compound C14) | 1.00 |
| PHASE B | |
| Xanthan Gum | 0.20 |
| Natrosol ® 250HHR (ethyl cellulose) | 0.50 |
| Butylene Glycol | 3.00 |
| Glycerin | 2.00 |
| PHASE C | |
| Sodium Stearoyl Lactylate | 0.10 |
| Glycerol Monostearate | 1.50 |
| Stearyl Alcohol | 1.50 |
| Isostearyl Palmitate | 3.00 |
| Silicone Fluid | 1.00 |
| Cholesterol | 0.25 |
| Sorbitan Stearate | 1.00 |
| Butylated Hydroxy Toluene | 0.05 |
| Vitamin E Acetate | 0.01 |

TABLE I-continued

| INGREDIENT | WEIGHT % |
|---|---|
| PEG-100 Stearate | 2.00 |
| Stearic Acid | 3.00 |
| Propyl Paraben | 0.10 |
| Parsol MCX ® | 2.00 |
| Caprylic/Capric Triglyceride | 0.50 |
| Hydroxycaprylic Acid | 0.01 |
| C12-15 Alkyl Octanoate | 3.00 |
| PHASE D | |
| Vitamin A Palmitate | 0.10 |
| Bisabolol | 0.01 |
| Vitamin A Acetate | 0.01 |
| Fragrance (20% Limonene and 3% alpha pinene) | 0.03 |
| Retinol 50C | 0.02 |
| Methanone, (1,1-dimethyl-3,3-dimethylbutylaminyl)tricyclo[$3.3.1.1^{3,7}$]dec-1-yl-(Compound C21) | 0.50 |

Example 30

A water-in-oil topical liquid make-up foundation according to invention is described in Table II below.

TABLE II

| INGREDIENT | WEIGHT % |
|---|---|
| PHASE A | |
| Cyclomethicone | 9.25 |
| Oleyl Oleate | 2.00 |
| Dimethicone Copolyol | 20.00 |
| PHASE B | |
| Talc | 3.38 |
| Pigment (Iron Oxides) | 10.51 |
| Spheron L-1500 (Silica) | 0.50 |
| PHASE C | |
| Synthetic Wax Durachem 0602 | 0.10 |
| Arachidyl Behenate | 0.30 |
| PHASE D | |
| Cyclomethicone | 1.00 |
| Trihydroxystearin | 0.30 |
| PHASE E | |
| Laureth-7 | 0.50 |
| Propyl Paraben | 0.25 |
| PHASE F | |
| Fragrance (50% limonene and 10% hexyl acetate) | 0.05 |
| PHASE G | |
| Water | balance |
| Methanone, (3-methyl-1-piperidinyl)tricyclo[$3.3.1.1^{3,7}$]dec-1-yl-(compound C14) | 3.00 |
| Methyl Paraben | 0.12 |
| Propylene Glycol | 8.00 |
| Niacinamide | 4.00 |
| Glycerin | 3.00 |
| Sodium Chloride | 2.00 |
| Sodium Dehydroacetate | 0.30 |

Example 31

An aerosol packaged foaming cleanser with a tricyclodecane amide and limonene as a major component of the fragrance is outlined in Table IV.

TABLE IV

| INGREDIENT | WEIGHT % |
|---|---|
| Sunflower Seed Oil | 10.00 |
| Glycerin | 10.00 |
| Maleated Soybean Oil | 5.00 |
| Silicone Urethane | 1.00 |
| Polyglycero-4 Oleate | 1.00 |
| Sodium C14-16 Olefin Sulfonate | 15.00 |
| Sodium Lauryl Ether Sulphate (25% active) | 15.00 |
| Cocoamidopropylbetaine | 15.00 |
| DC 1784 ® (Silicone Emulsion 50%) | 5.00 |
| Polyquaternium-11 | 1.00 |
| Methanone, (3-methyl-1-piperidinyl)tricyclo[$3.3.1.1^{3,7}$]dec-1-yl-(compound C14) | 1.00 |
| Fragrance (20% Limonene) | 1.00 |
| Water | Balance |

Example 32

A disposable, single use personal care towelette product is described according to the present invention. A 70/30 polyester/rayon non-woven towelette is prepared with a weight of 1.8 grams and dimensions of 15 cm by 20 cm. Onto this towelette is impregnated 1.0 grams of a composition including a tricyclodecane amide and a fragrance having 20% limonene and 20% alpha pinene as outlined in Table V below.

TABLE V

| INGREDIENT | WEIGHT % |
|---|---|
| Methanone, (1,1-dimethyl-3,3-dimethylbutylaminyl)tricyclo[$3.3.1.1^{3,7}$] dec-1-yl-(Compound C21) | 4.00 |
| Glycerin | 12.00 |
| Hexylene Glycol | 2.00 |
| Disodium Capryl Amphodiacetate | 1.00 |
| Gluconolactone | 0.90 |
| Silicone Microemulsion | 0.85 |
| Witch Hazel | 0.50 |
| PEG-40 Hydrogenated Castor Oil | 0.50 |
| Fragrance (20% Limonene and 20% alpha pinene) | 0.20 |
| Vitamin E Acetate | 0.001 |
| Water | Balance |

Example 33

A series of experiments were conducted to evaluate release and prolonged scent generation of typical components of a perfume mixture. Samples were prepared by mixing 0.5 wt % of tricyclodecane amide and 1% soybean oil in water. In the examples with perfume, samples included with 0.1% of a fragrance oil. This model fragrance oil was a mixture of components including but not limited to phenylethyl alcohol, benzyl acetate, alpha pinene, beta pinene, hexyl acetate, limonene, (+)-citronellal, dihydromyrcenol, alpha citronellol, beta citronellol, genaniol, and lilial. Control sample was made with 0.1 wt. % of the same model fragrance, 1% soybean oil in water without tricyclodecane amide.

Samples were analyzed by gas chromatography (GC) analysis of headspace gases. In this procedure, the equipment utilized was a solid phase microextraction (SPME) system employing gas chromatography (GC) 6890/mass spectrometry (MS) 5973/flame ionization detector (FID). This equipment measured relative perfume compound abundance in the headspace over the above mentioned mixture, as well as over the control sample. Two grams of the mixture was prepared in 20 ml GC headspace sampling vials sealed with caps having septums (from Gerstel, Inc.). The GC column was a HP-5MS column from Agilent (inner diameter 0.25 mm, length 30 m, stationary phase thickness 0.25 um). The GC conditions were as follows: Injector in splitless mode with helium gas as carrier gas. Injection port was heated to 250° C., purge flow to split vent 50 ml/min at zero minutes. Column was in constant flow mode with 1.3 ml/min flow rate. Oven temperature ramp: hold at 75° C. for 2 minutes, then increase oven temperature at a rate of 6° C./min to 100° C., 1.5° C./min to 150° C., 3° C./min to 190° C., 30° C./min to 300° C. and hold for 2 minutes. MS conditions were: solvent delay for 0.5 minutes, scan starting from low mass 35 to high mass 300. Autosampler's conditions were: No incubation (all experiments done in room temperature). SPME fibre was inserted into the sample headspace for a 5 minute extraction and then injected to the injector for a 15 minute desorption.

Results of the experiments are reported in Table II-VIII below. In the Tables below, normalized headspace is calculated as fragrance headspace concentration of oil/water mixture containing tricyclodecane amide (Formula I and Formula II) or linear amide divided by that of control (oil/water mixture without amide). A lower normalized headspace concentration indicates a lower volatility of the fragrance compound and therefore potentially prolonged release. Reduction ratio is that of the control headspace divided by that of sample with amide. The higher the reduction ratio, the more long lasting the fragrance compound upon addition of tricyclodecane amide.

TABLE VI

| chemical name | CAS | Control | | Compound C14 | | | Compound C10 | | |
| --- | --- | --- | --- | --- | --- | --- | --- | --- | --- |
| | | Normalized headspace concentration | Stdev* | Normalized headspace concentration | Stdev* | Reduction ratio | Normalized headspace concentration | Stdev* | Reduction ratio |
| alpha pinene | 80-56-8 | 1 | 0.05 | 0.41 | 0.05 | 2.44 | 0.22 | 0.01 | 4.55 |
| beta pinene | 127-91-3 | 1 | 0.04 | 0.50 | 0.06 | 2.00 | 0.25 | 0.02 | 4.00 |
| hexyl acetate | 142-92-7 | 1 | 0.04 | 0.72 | 0.03 | 1.39 | 0.75 | 0.01 | 1.33 |
| limonene | 138-86-3 | 1 | 0.05 | 0.50 | 0.07 | 2.00 | 0.25 | 0.02 | 4.00 |
| dihydromyrcenol | 18479-58-8 | 1 | 0.03 | 0.68 | 0.02 | 1.47 | 0.76 | 0.03 | 1.32 |
| (+)-citronellal | 106-23-0 | 1 | 0.01 | 0.5 | 0.03 | 2.00 | 0.64 | 0.05 | 1.56 |
| alpha citronellol | 106-22-9 | 1 | 0.02 | 0.41 | 0.01 | 2.44 | 0.60 | 0.06 | 1.67 |
| beta citronellol | 7540-51-4 | 1 | 0.02 | 0.47 | 0.004 | 2.13 | 0.64 | 0.06 | 1.56 |
| geraniol | 106-24-1 | 1 | 0.04 | 0.81 | 0.04 | 1.23 | 0.71 | 0.06 | 1.41 |
| lilial | 80-54-6 | 1 | 0.02 | 0.72 | 0.02 | 1.39 | 0.83 | 0.06 | 1.20 |
| Comparative | | | | | | | | | |
| benzyl acetate | 140-11-4 | 1 | 0.05 | 0.97 | 0.05 | 1.03 | 0.89 | 0.04 | 1.12 |
| PEA | 60-12-8 | 1 | 0.13 | 1.34 | 0.28 | 0.75 | 0.90 | 0.15 | 1.11 |

*Standard deviation

TABLE VII

| chemical name | CAS number | Control | | Compound C21 | | |
| --- | --- | --- | --- | --- | --- | --- |
| | | Normalized headspace concentration | Stdev* | Normalized headspace concentration | Stdev* | Reduction ratio |
| alpha pinene | 80-56-8 | 1 | 0.05 | 0.44 | 0.10 | 2.27 |
| beta pinene | 127-91-3 | 1 | 0.04 | 0.54 | 0.12 | 1.85 |
| hexyl acetate | 142-92-7 | 1 | 0.04 | 0.80 | 0.03 | 1.25 |
| limonene | 138-86-3 | 1 | 0.05 | 0.53 | 0.11 | 1.89 |
| (+)-citronellal | 106-23-0 | 1 | 0.01 | 0.65 | 0.05 | 1.54 |
| Comparative | | | | | | |
| dihydromyrcenol | 18479-58-8 | 1 | 0.03 | 0.88 | 0.08 | 1.14 |
| PEA | 60-12-8 | 1 | 0.13 | 1.21 | 0.33 | 0.83 |
| benzyl acetate | 140-11-4 | 1 | 0.05 | 1.00 | 0.20 | 1.00 |
| alpha citronellol | 106-22-9 | 1 | 0.02 | 0.86 | 0.11 | 1.16 |
| beta citronellol | 7540-51-4 | 1 | 0.02 | 0.85 | 0.09 | 1.18 |
| geraniol | 106-24-1 | 1 | 0.04 | 0.95 | 0.09 | 1.05 |
| lilial | 80-54-6 | 1 | 0.02 | 1.06 | 0.09 | 0.97 |

*Standard deviation

TABLE VIII

| chemical name | CAS number | Control Normalized headspace concentration | Stdev* | octadecanamide Normalized headspace concentration | Stdev* | Reduction ratio |
|---|---|---|---|---|---|---|
| alpha pinene | 80-56-8 | 1 | 0.08 | 1.21 | 0.19 | 0.83 |
| beta pinene | 127-91-3 | 1 | 0.06 | 1.05 | 0.13 | 0.95 |
| hexyl acetate | 142-92-7 | 1 | 0.07 | 1.11 | 0.09 | 0.90 |
| limonene | 138-86-3 | 1 | 0.07 | 1.12 | 0.16 | 0.89 |
| dihydromyrcenol | 18479-58-8 | 1 | 0.11 | 1.06 | 0.08 | 0.94 |
| PEA | 60-12-8 | 1 | 0.19 | 1.07 | 0.12 | 0.93 |
| (+)-citronellal | 106-23-0 | 1 | 0.1 | 1.09 | 0.11 | 0.92 |
| benzyl acetate | 140-11-4 | 1 | 0.18 | 1.12 | 0.14 | 0.89 |
| alpha citronellol | 106-22-9 | 1 | 0.12 | 1.04 | 0.10 | 0.96 |
| beta citronellol | 7540-51-4 | 1 | 0.11 | 1.03 | 0.08 | 0.97 |
| geraniol | 106-24-1 | 1 | 0.17 | 1.05 | 0.15 | 0.95 |
| lilial | 80-54-6 | 1 | 0.12 | 1.04 | 0.11 | 0.96 |

*Standard deviation

Evident from the results in Tables II-VIII is that certain fragrance ingredients were particularly suppressed into the headspace by the presence of the tricyclodecane amide. These ingredients are alpha pinene, beta pinene, hexyl acetate, limonene, (+)-citronellal, dihydromyrcenol, alpha citronellol, beta citronellol, geraniol, lilial for tricyclodecane amides of Formula I (e.g. Compounds C10 and C 14,). Tricyclodecanes of Formula II (e.g., compound C21) had this effect on a subset of perfumes: alpha pinene, beta pinene, hexyl acetate, limonene, (+)-citronellal. Linear amides (such as Octadecanamide) with similar number of carbons (e.g., octadecanamide) did not have this effect.

Long lasting fragrance is one of the most desirable sensory benefit from various personal care product forms (e.g., lotion, antiperspirant/deodorant, etc.). Due to high volatility of most fragrance compounds, after immediate application of most personal care product, perfume of high volatility will flash away, which leads to weaker or no perfume impact over time, or change of the hedonic characters of the originally designed perfume. It is surprising that tricyclodecanes of Formula I and Formula II suppress the volatility of selected perfume compounds (e.g., lower headspace concentration), which will lead to a slower release of those selected perfume compounds and therefore a longer lasting effect.

While described in terms of the presently preferred embodiments, it is to be understood that such disclosure is not to be interpreted as limiting. Various modifications and alterations will no doubt occur to one skilled in the art after having read the above disclosure. Accordingly, it is intended that the appended claims be interpreted as covering all such modifications and alterations as falling within the true spirit and scope of the invention.

The invention claimed is:

1. A personal care water and oil composition comprising:
   (i) from about 0.000001 to about 2% of a fragrance component selected from the group consisting of alpha pinene, beta pinene, hexyl acetate, limonene, (+)-citronellal, dihydromyrcenol, alpha citronellol, beta citronellol, geraniol, lilial, and mixtures thereof;
   (ii) from about 0.0001% to about 20% by weight of a tricyclodecane amide, wherein the tricyclodecane amide is selected from:

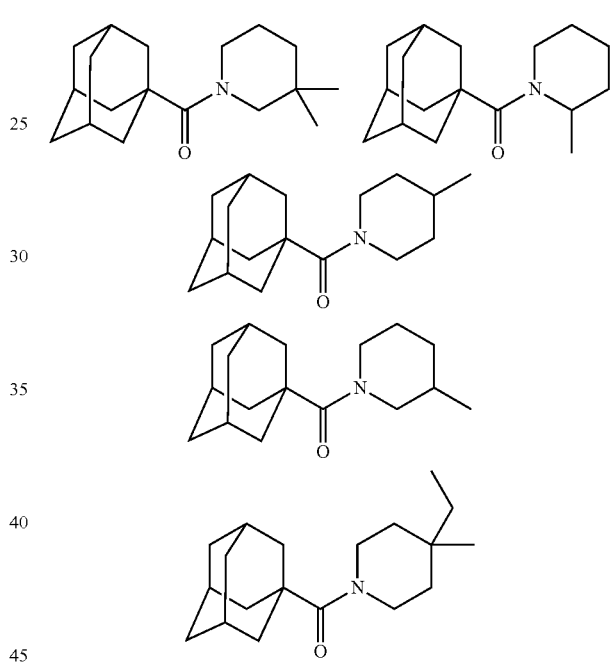

and
Formula I:

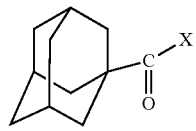

Formula I where X is selected from:

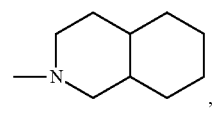

Xf

-continued

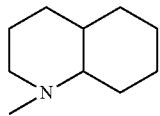

and (iii) a cosmetically acceptable carrier.

2. The composition according to claim 1 which is selected from the group consisting of leave-on or rinse-off skin lotions and creams, shower gels, antiperspirants, deodorants, dental products, shave creams, depilatories, lipsticks, foundations, mascara, sunless tanner and sunscreen lotions.

3. A personal care water and oil composition comprising:
(i) from about 0.000001 to about 2% of a fragrance component selected from the group consisting of alpha pinene, beta pinene, hexyl acetate, limonene, (+)-citronellal, and mixtures thereof;
(ii) from about 0.01% to about 30% by weight of a tricyclodecane amide of Formula II

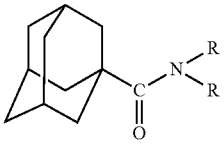

Formula II wherein each R is independently hydrogen, methyl, ethyl or $C_3$ to $C_{10}$, linear or branched alkyl, with the proviso that both R groups are not simultaneously hydrogen; and
(ii) a cosmetically acceptable carrier.

4. The composition according to claim 3 which is selected from the group consisting of leave-on skin lotions and creams, shower gels, antiperspirants, deodorants, dental products, shave creams, depilatories, lipsticks, foundations, mascara, sunless tanner and sunscreen lotions.

5. The composition according to claim 2, further comprising a skin lightening ingredient selected from the group consisting of placental extract, lactic acid, niacinamide, arbutin, kojic acid, ferulic acid, resorcinol and derivatives including 4-substituted resorcinols, and mixtures thereof.

6. The composition according to claim 2, further comprising a preservative selected from the group consisting of phenoxyethanol, methyl paraben, propyl paraben, imidazolidinyl urea, sodium dehydroacetate, caprylyl glycol and benzyl alcohol.

7. The composition according to claim 6 further comprising octocrylene and caprylyl glycol.

8. The composition according to claim 2, further comprising a sunscreen.

9. The composition according to claim 2 further comprising vitamins selected from the group consisting of Vitamin A (retinol), Vitamin B2, Vitamin B3 (niacinamide), Vitamin B6, Vitamin C, Vitamin E and Biotin, and derivatives thereof.

10. The composition according to claim 9 wherein the vitamin is Vitamin B3 (niacinamide).

11. The composition according to claim 8 further comprising a sunscreen selected from the group consisting of ethylhexyl p-methoxycinnamate, Avobenzene, octylsalicylate, tetraphthalylidene dicamphor sulfonic acid, benzophenone-4, benzophenone-3 (Oxybenzone) and octocrylene.

12. A method of prolonging the scent of a volatile fragrance, the method comprising applying to human body the composition of claim 2.

* * * * *